United States Patent
May

(10) Patent No.: US 10,792,281 B2
(45) Date of Patent: *Oct. 6, 2020

(54) LEVOCETIRIZINE AND MONTELUKAST IN THE TREATMENT OF INFLAMMATION MEDIATED CONDITIONS

(71) Applicant: IRR, Inc., Santa Barbara, CA (US)

(72) Inventor: Bruce Chandler May, Santa Barbara, CA (US)

(73) Assignee: IRR, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,573

(22) Filed: Dec. 18, 2018

(65) Prior Publication Data

US 2019/0201393 A1 Jul. 4, 2019

Related U.S. Application Data

(63) Continuation of application No. 15/895,918, filed on Feb. 13, 2018, now Pat. No. 10,195,193, which is a continuation of application No. 15/450,840, filed on Mar. 6, 2017, now Pat. No. 9,925,183, which is a continuation of application No. PCT/US2015/049767, filed on Sep. 11, 2015.

(60) Provisional application No. 62/050,668, filed on Sep. 15, 2014.

(51) Int. Cl.
| | |
|---|---|
| *A61K 31/49* | (2006.01) |
| *A61K 31/497* | (2006.01) |
| *A61K 31/495* | (2006.01) |
| *A61K 31/47* | (2006.01) |
| *A61P 25/00* | (2006.01) |
| *A61P 25/16* | (2006.01) |
| *A61P 25/28* | (2006.01) |
| *A61K 45/06* | (2006.01) |

(52) U.S. Cl.
CPC ............ *A61K 31/495* (2013.01); *A61K 31/47* (2013.01); *A61K 45/06* (2013.01); *A61P 25/00* (2018.01); *A61P 25/16* (2018.01); *A61P 25/28* (2018.01); *Y02A 50/385* (2018.01); *Y02A 50/387* (2018.01); *Y02A 50/393* (2018.01); *Y02A 50/395* (2018.01); *Y02A 50/411* (2018.01)

(58) Field of Classification Search
CPC .............................. A61K 31/495; A61K 31/47
USPC ............................................. 514/252.12, 311
See application file for complete search history.

(56) References Cited

U.S. PATENT DOCUMENTS

| | | |
|---|---|---|
| 4,801,612 A | 1/1989 | Wei et al. |
| 5,147,637 A | 9/1992 | Wright et al. |
| 5,211,958 A | 5/1993 | Akkerboom et al. |
| 5,540,225 A | 7/1996 | Schutt |
| 6,384,038 B1 | 5/2002 | Rubin |
| 6,790,849 B2 | 9/2004 | Rubin |
| 7,166,640 B2 | 1/2007 | Berg |
| 7,186,555 B1 | 3/2007 | Tracey et al. |
| 7,291,331 B1 | 11/2007 | Croft et al. |
| 7,589,076 B2 | 9/2009 | Rieger et al. |
| 9,044,479 B2 | 6/2015 | May |
| 9,522,148 B2 | 12/2016 | May |
| 9,669,025 B2 | 6/2017 | May |
| 9,669,026 B2 | 6/2017 | May |
| 9,925,183 B2 | 3/2018 | May |
| 9,937,166 B2 | 4/2018 | May |
| 10,195,193 B2 | 2/2019 | May |
| 10,201,537 B2 | 2/2019 | May |
| 10,206,919 B2 | 2/2019 | May |
| 10,537,568 B2 | 1/2020 | May |
| 2001/0033872 A1 | 10/2001 | Corson et al. |
| 2002/0052312 A1 | 5/2002 | Reiss et al. |
| 2004/0180868 A1 | 9/2004 | Mullally |
| 2005/0256131 A1 | 11/2005 | Coester |
| 2006/0263350 A1 | 11/2006 | Lane |
| 2007/0020352 A1 | 1/2007 | Tripp et al. |
| 2007/0025987 A1 | 2/2007 | Brunetta |
| 2007/0225285 A1 | 9/2007 | Hutchinson et al. |
| 2007/0244128 A1 | 10/2007 | Hutchinson et al. |
| 2008/0260644 A1 | 10/2008 | Cohen |
| 2010/0305080 A1 | 12/2010 | O'Shea |
| 2012/0040892 A9 | 2/2012 | Zimmer et al. |
| 2012/0053563 A1 | 3/2012 | Du |
| 2012/0071509 A1 | 3/2012 | Gore et al. |

(Continued)

FOREIGN PATENT DOCUMENTS

| | | |
|---|---|---|
| CA | 2 802 853 | 12/2011 |
| CN | 102 895 661 | 1/2013 |

(Continued)

OTHER PUBLICATIONS

Bernier et al., "Consensus Guidelines for the Management of Radiation Dermatitis and Coexisting Acne-Like Rash in Patients Receiving Radiotherapy Plus EGFR Inhibitors for the Treatment of Squamous Cell Carcinoma of the Head and Neck", Annals of Oncology, vol. 19, 2008, pp. 142-149.

(Continued)

*Primary Examiner* — Raymond J Henley, III

(74) *Attorney, Agent, or Firm* — Knobbe, Martens, Olson & Bear, LLP

(57) ABSTRACT

The embodiments described herein include methods and formulations for treating viruses and diseases that are exacerbated by inflammatory responses in the body. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

16 Claims, 2 Drawing Sheets

(56) References Cited

U.S. PATENT DOCUMENTS

| | | |
|---|---|---|
| 2012/0190691 A1 | 7/2012 | Bouyssou et al. |
| 2012/0263764 A1 | 10/2012 | Watson |
| 2013/0011395 A1 | 1/2013 | Spies et al. |
| 2013/0029949 A1 | 1/2013 | Hoffmann et al. |
| 2013/0030000 A1 | 1/2013 | Chobanian et al. |
| 2013/0030009 A1 | 1/2013 | Harish et al. |
| 2013/0085124 A1 | 4/2013 | May |
| 2015/0231133 A1 | 8/2015 | May |
| 2015/0352101 A1 | 12/2015 | May |
| 2015/0352102 A1 | 12/2015 | May |
| 2015/0352103 A1 | 12/2015 | May |
| 2015/0352104 A1 | 12/2015 | May |
| 2016/0175301 A1 | 6/2016 | May |
| 2017/0056395 A1 | 3/2017 | May |
| 2017/0231980 A1 | 8/2017 | May |
| 2017/0296534 A1 | 10/2017 | May |
| 2017/0368059 A1 | 12/2017 | May |
| 2018/0185357 A1 | 7/2018 | May |
| 2019/0091218 A1 | 3/2019 | May |
| 2019/0201392 A1 | 7/2019 | May |
| 2019/0298714 A1 | 10/2019 | May |
| 2020/0101067 A1 | 4/2020 | May |

FOREIGN PATENT DOCUMENTS

| | | |
|---|---|---|
| CN | 103 505 731 | 1/2014 |
| EP | 1 769 797 | 4/2007 |
| EP | 2 520 292 | 7/2012 |
| JP | 2001-511134 | 8/2001 |
| JP | 2001-526232 | 12/2001 |
| JP | 2002-511425 | 4/2002 |
| JP | 2004-536097 | 12/2004 |
| JP | 2009-520711 | 5/2009 |
| JP | 2009-525952 | 7/2009 |
| JP | 2011-500847 | 1/2011 |
| JP | 2012-519207 | 8/2012 |
| JP | 2013-528654 | 7/2013 |
| KR | 10-2001-0033485 | 4/2001 |
| RU | 2442789 | 6/2010 |
| WO | WO 95/009652 | 4/1995 |
| WO | WO 99/032125 | 7/1999 |
| WO | WO 99/052553 | 10/1999 |
| WO | WO 03/002098 | 1/2003 |
| WO | WO 03/002109 | 1/2003 |
| WO | WO 03/101434 | 12/2003 |
| WO | WO 2006/010283 | 2/2006 |
| WO | WO 2008/100539 | 8/2008 |
| WO | WO 2008/106429 | 9/2008 |
| WO | WO 2009/022327 | 2/2009 |
| WO | WO 2009/055729 | 4/2009 |
| WO | WO 2010/107404 | 9/2010 |
| WO | WO 2011/003074 | 1/2011 |
| WO | WO 2011/041462 | 4/2011 |
| WO | WO 2011/094209 | 8/2011 |
| WO | WO 2011/159821 | 12/2011 |
| WO | WO 2012/064301 | 5/2012 |
| WO | WO 2012/064305 | 5/2012 |
| WO | WO 2012/092594 | 7/2012 |
| WO | WO 2013/012199 | 1/2013 |
| WO | WO 2013/013490 | 1/2013 |
| WO | WO 2013/148366 | 10/2013 |
| WO | WO 2014/090990 | 6/2014 |
| WO | WO 2014/164281 | 10/2014 |
| WO | WO 2014/164282 | 10/2014 |
| WO | WO 2014/164285 | 10/2014 |
| WO | WO 2014/164299 | 10/2014 |
| WO | WO 2016/044095 | 3/2016 |
| WO | WO 2017/210417 | 12/2017 |

OTHER PUBLICATIONS

Deb et al., "Pathophysiologic Mechanisms of Acute Ischemic Stroke: An Overview with Emphasis on Therapeutic Significance Beyond Thrombolysis", Pathophysiology, 2010, vol. 17, pp. 197-218.
Elting et al., "Comparison of Serum S-100 Protein Levels Following Stroke and Traumatic Brain Injury", Journal of the Neurological Sciences, 2000, vol. 181, pp. 104-110.
International Preliminary Report on Patentability received in PCT Application No. PCT/US2015/049767, dated Mar. 30, 2017 in 9 pages.
International Search Report and Written Opinion received in PCT Application No. PCT/US2015/049767, dated Jan. 21, 2016 in 11 pages.
Medzhitov, Ruslan, "Origin and Physiological Roles of Inflammation," Nature, vol. 454, Jul. 24, 2008, pp. 428-435.
Murdoch et al., "Chronic Inflammation and Asthma", Mutation Research: Fundamental and Molecular Mechanisms of Mutagenesis, 2010, vol. 690, pp. 24-39.
Pellicane, MD, et al., "Calorie and Protein Intake in Acute Rehabilitation Inpatients with Traumatic Spinal Cord Injury Versus Other Diagnoses", Topics in Spinal Cord Injury Rehabilitation, 2013, vol. 19, No. 3, pp. 229-235.
Quercia et al., "Adalimumab Desensitization after Anaphylactic Reaction", Allergy, 2010, vol. 65, No. 92, pp. 242-243.
Rosen et al., "New Approaches to Radiation Protection," Frontiers in Oncology, Jan. 20, 2015, vol. 4, No. 381, pp. 1-15.
Vasculitis Foundation, http://vasculitisfoundation.org/education/forms/urticarial-vasculitis/, 2017.
Zappalà et al., "Traumatic brain injury and the frontal lobes: What can we gain with diffusion tensor imaging?" Cortex, 2011, pp. 1-10.
Al-Ahmad, Mona, "Omalizumab Therapy in Three Patients with Chronic Autoimmune Urticaria", Annals of Saudi Medicine, vol. 30, No. 6, Nov.-Dec. 2010, pp. 478-481.
Athanasiadis et al., "Urticarial Vasculitis With a Positive Autologous Serum Skin Test: Diagnosis and Successful Therapy", Allergy, 2006, vol. 61, pp. 1484-1485.
Bisgaard Hans, "A Randomized Trial of Montelukast in Respiratory Syncytial Virus Postbronchiolitis", American Journal of Respiratory and Critical Care Medicine, 2003, vol. 167, No. 3, pp. 379-383.
Borish MD, Larry, "Allergic Rhinitis: Systemic Inflammation and Implications for Management", The Journal of Allergy and Clinical Immunology, Dec. 1, 2003, pp. 1021-1031.
Ciebieada, MD et al., "Montelukast with Desloratadine or Levocetirizine for the Treatment of Persistent Allergic Rhinitis", Annals of Allergy, Asthma & Immunology, Nov. 2006, vol. 97, pp. 664-671.
Clinical Surgery, 1999, Oct. 3, vol. 54, No. 11, Special Issue, pp. 13-15.
Dávila et al., "Effect of H1 Antihistamines Upon the Cardiovascular System", Journal of Investigational Allergology and Clinical Immunology, 2006, vol. 16, No. 1, pp. 13-23.
Eccles, Ron, "Understanding the Symptoms of the Common Cold and Influenza", The Lancet Infectious Diseases, R(1) Nov. 2005, vol. 5, No. 11, pp. 718-725.
El-Shanawany et al., "Clinical Immunology Review Series: An Approach to the Patient with Anaphylaxis", British Society for Immunology, Clinical and Experimental Immunology, 2008, vol. 153, pp. 1-9.
Fedson, David, "A Practical Treatment for Patients with Ebola Virus Disease", Journal of Infectious Diseases, Aug. 25, 2014, pp. 5.
Fedson, David, "Treating Influenza with Statins and Other Immunomodulatory Agents", Antiviral Research, Sep. 2013, vol. 99, No. 3, pp. 417-435.
Glantschnig et al., "Mass Fraction Profiling Based on X-Ray Tomography and its Application to Characterizing Porous Silica Boules", Applied Optics, Mar. 15, 1987, vol. 26, No. 6, pp. 983-989.
Heneka et al., "Innate Immune Activation in Neurodegenerative Disease", Nature Reviews, Jul. 2014, vol. 14, pp. 463-477.
Hong et al., "Urticaria and Angioedema", Cleveland Clinic—Center for Continuing Education, Aug. 2010, pp. 11.
Ingelsson et al., "Nationwide Cohort Study of the Leukotriene Receptor Antagonist Montelukast and Incident or Recurrent Cardiovascular Disease", Journal of Allergy and Clinical Immunology, Mar. 2012, vol. 129, No. 3, pp. 702-707.e2.

(56) References Cited

OTHER PUBLICATIONS

Jang et al., "Levoceterizine Inhibits Rhinovirus-Induced ICAM-1 and Cytokine Expression and Viral Replication in Airway Epithelial Cells", Antiviral Research, Mar. 2009, vol. 81, No. 3, pp. 226-233.
Jensen et al., "Sensing of RNA Viruses: a Review of Innate Immune Receptors Involved in Recognizing RNA Virus Invasion", Journal of Virology, Mar. 2012, vol. 86, No. 6, pp. 2900-2910.
Jianxin et al., "Therapeutic Effectiveness Analysis of Montelukast in Therapy of Anaphylactic Purpura", Journal of Clinical and Experimental Medicine, May 2010, vol. 9, No. 10, pp. 782-783.
Khoury, MD et al., "Effect of Montelukast on Bacterial Sinusitis in Allergic Mice", Annals of Allergy, Asthma & Immunology, Sep. 2006, vol. 97, No. 3, pp. 329-335.
Kozel et al., "Chronic Urticaria: Aetiology, Management and Current and Future Treatment Options," Drugs, 2004, vol. 64, No. 22, pp. 2515-2536.
Kronenberg et al., "Symptomatic Treatment of Uncomplicated Lower Urinary Tract Infections in the Ambulatory Setting: Randomised, Double Blind Trial", BMJ, 2017, vol. 359, No. J4787, pp. 10.
Kuna et al., "Two Phase II Randomized Trials on the CR Th2 Antagonist AZD1981 in Adults with Asthma", Drug Design, Development and Therapy, 2016, vol. 10, pp. 2759-2770.
Kurowski et al., "Montelukast Plus Cetirizine in the Prophylactic Treatment of Seasonal Allergic Rhinitis: Influence of Clinical Symptoms and Nasal Allergic Inflammation", Allergy, 2004, vol. 59, pp. 280-288.
Lishchuk-Yakymovych et al., "Positive Correlation Between Serum IL-5 and TNF-alpha Levels and Churg-Strauss Syndrome Activity in Patients Successfully Treated with Motelukast", Journal of Allergy and Clinical Immunology, Entry 295, Feb. 2012, p. 1.
Luthra et al., "Mutual Antagonism between the Ebola Virus VP35 Protein and the RIG-1 Activator PACT Determines Infection Outcome", Cell Host Microbe, Jul. 17, 2013, vol. 14, No. 1, pp. 1-23.
Mansi et al., "ANCA-Associated Small-Vessel Vasculitis", American Family Physician, Apr. 15, 2002, vol. 65, No. 8, pp. 1615-1620.
Mathiesen et al., "On the Mechanism of Interaction of Potent Surmountable and Insurmountable Antagonists with the Prostaglandin D2 Receptor CRTH2", Molecular Pharmacology, 2006, vol. 69, No. 4, pp. 1441-1453.
May, B. Chandler, "A Proposed Model for the Treatment of Acute Inflammation", Mazatlán, Mexico, LXIV Conference of the Mexican College of Clinical Immunology and Allergy, May 29, 2010, pp. 3.
May, B. Chandler, "Contemporary Treatment of Influenza", Santa Barbara, CA, 25th Annual Infectious Disease Conference, Dec. 18, 2009, pp. 36.
McElroy et al., Ebola Hemorrhagic Fever: Novel Biomarker Correlates of Clinical Outcome, Journal of Infectious Disease, Aug. 15, 2014, vol. 210, No. 4, pp. 558-566.
McKinney et al., "The Immunopatholgy of ANCA-Associated Vasculitis", Semin Immunopathol, 2014, vol. 36, pp. 461-478.
Min et al., "Levocetirizine Inhibits Rhinovirus-Induced Bacterial Adhesion to Nasal Epithelial Cells Through Down-Regulation of Cell Adhesion Molecules", Annals of Allergy, Asthma and Immunology, 2012, vol. 108, pp. 44-48.
Modrykamien, MD et al., "The Acute Respiratory Distress Syndrome", Proceedings (Baylor University Medical Center) 2015, vol. 28, No. 2, pp. 163-171.
Moiz et al., "Formulation and Evaluation of Bilayered Tablets of Montelukast and Levocetrizine Dihydrocholoride Using Natural and Synthetic Polymers", International Journal of Drug Delivery 3, Jan. 2011, pp. 597-618.
Muller, Barbara A., "Urticaria and Angioedema: A Practical Approach", American Family Physician, 2004, vol. 69, No. 5, pp. 1123-1128.
Namazi, M.R. "Cetirizine and Allopurinol as Novel Weapons Against Cellular Autoimmune Disorders", International Immunopharmacology, 2004, vol. 4, pp. 349-353.
Nederkoorn et al., "Preventive Antibiotics in Stroke Study: Rationale and Protocol for a Randomised Trial", International Journal of Stroke, Apr. 2011, vol. 6, pp. 159-163.

Nonaka et al., "Prolonged Activation of NF-κB Following Traumatic Brain Injury in Rats", Journal of Neurotrauma, Nov. 1999, vol. 16, No. 11, pp. 1023-1034.
Parker, MD et al., "A 48 Year Old Man with Recurrent Sinusitis, 1 Year Later", JAMA, Clinical Crossroads Update, Jan. 24/31, 2001, vol. 285, No. 4, p. 462.
Peroni et al., "Combined Cetirizine-Montelukast Preventative Treatment for Food-Dependent Exercise-Induced Anaphylaxis", Annals of Allery, Asthma, & Immunology, Mar. 2010, vol. 104, pp. 272-273.
Popov et al., "A Comparison of Levocetirizine and Desloratadine in the Histamine-Induced Wheal and Flare Response in Human Skin in Vivo", Inflammatory Research, Jun. 2006, vol. 55, No. 6, pp. 241-244.
"Prostaglandin DP2 receptor", Wikipedia, <https://en.wikipedia.org/wiki/Prostaglandin_DP2_receptor>, Aug. 25, 2017, pp. 9.
Pushparaj et al., "The Cytokine Interleukin-33 Mediates Anaphylactic Shock", with Retraction and Correction, Proceeding of the National Academy of Sciences of the United States of America (PNAS), Jun. 16, 2009, vol. 106, No. 24, pp. 9773-9778.
Radlińska et al., "Montelukast—Recent Advances in Determining the Role of Leukotriene Inhibitor in Allergic Diseases", International Review of Allergology and Clinical Immunology, Jan. 2011, vol. 17:1-2, pp. 35-39.
Roumestan et al., "Histamine H1-receptor antagonists inhibit nuclear factor-kappaB and activator protein-1 activities via H1-receptor-dependent and -independent mechanisms", Clinical and Experimental Allergy, Jun. 2008, vol. 38, No. 6, pp. 947-956.
Schad et al., "Effect of Montelukast on Pro-inflammatory Cytokine Production During Naturally Acquired Viral Upper Respiratory Infections (vURIs) in Adults", Journal of Allergy and Clinical Immunology, Elsevier, Amsterdam, NL, Feb. 2008, vol. 121, No. 2, p. S74.
Singh-Franco et al., "Levocetirizine for the Treatment of Allergic Rhinitis and Chronic Idiopathic Urticaria in Adults and Children", Clinical Therapeutics, vol. 31, No. 8, Aug. 2009, pp. 1664-1687.
Spiropoulou et al., "RIG-I Activation Inhibits ebolavirus Replication", Virology, 2009, 392, pp. 11-15.
Taber's® Cyclopedic Medical Dictionary, "Trauma", 18th Edition, 1997, pp. 1988-1989.
Tang, Angela, "A Practical Guide to Anaphylaxis", American Family Physician, Oct. 1, 2013, vol. 68, No. 7, pp. 1325-1333.
Tillement et al., "Compared Pharmacological Characteristics in Humans of Racemic Cetirizine and Levocetirizine, Two Histamine H1-Receptor Antagonists", Biochemical Pharmacology, 2003, pp. 1123-1126.
Tillie-Leblond et al., "Relation Between Inflammation and Symptoms in Asthma", Allergy, vol. 64, No. 3, Mar. 1, 2009, pp. 354-367.
Wong et al., "Characterization of Host Immune Responses in Ebola Virus Infections", Expert Review of Clinical Immunology, 2014, vol. 10, No. 6, pp. 781-790.
Wu et al., "Add-On Therapy with Montelukast in the Treatment of Henoch-Schönlein Purpura", Pediatrics International, 2014, vol. 56, pp. 315-322.
Yu et al., "Montelukast, a Cysteinyl Leukotriene Receptor-1 Antagonist, Dose- and Time-Dependently Protects Against Focal Cerebral Ischemia in Mice", Pharmacology, Jan. 2005, vol. 73, No. 1, pp. 31-40.
Zana, Larry, "Qrono—Reformulating known, approved drugs", as printed Jun. 23, 2014, pp. 12.
Zhang et al., "Contrastive Observation of Loratadine and Cetirizine in Therapy of Anaphylactic Purpura", Chinese Remedies & Clinics, May 2008, pp. 65-66.
Lai et al., "Montelukast Targeting the Cysteinyl Leukotriene Receptor 1 Ameliorates Aβ1-42-Induced Memory Impairment and Neuroinflammatory and Apoptotic Responses in Mice", Neuropharmacology, Apr. 2014, vol. 79, pp. 707-714.
Garau et al., "Radiobiology of the Acute Radiation Syndrome", Reports of Practical Oncology and Radiotherapy, 2011, vol. 16, pp. 123-130.
Mathis et al., "Role of Leukotriene B4 Receptors in Rheumatoid Arthritis", Autoimmunity Reviews, Nov. 2007, vol. 7, No. 1, pp. 12-17.

(56) References Cited

OTHER PUBLICATIONS

Permin et al., "Possible Role of Histamine in Rheumatoid Arthritis", Allergy, 1981, vol. 36, pp. 435-436.
Williams et al., "Animal Models and Medical Countermeasures Development for Radiation-Induced Lung Damage: Report from an NIAID Workshop", Radiation Research, 2012, vol. 177, No. 5, pp. 25-39.
Wilson, D.C., "Effect of an Anti-Histamine in Rheumatoid Arthritis", Hospital for Rheumatic Diseases, Strathpeffer, Nov. 20, 1952, pp. 38-39.

FIG. 1

LEVOCETIRIZINE AND MONTELUKAST IN THE TREATMENT OF INFLAMMATION MEDIATED CONDITIONS

CROSS-REFERENCE TO RELATED APPLICATIONS

This patent application is a continuation of U.S. patent application Ser. No. 15/895,918, now U.S. Pat. No. 10,195,193, filed Feb. 13, 2018, of which is a continuation of U.S. patent application Ser. No. 15/450,840, now U.S. Pat. No. 9,925,183, filed Mar. 6, 2017, which is a continuation of PCT Patent Application No. PCT/US2015/049767, filed Sep. 11, 2015, which claims the benefit of priority to U.S. Provisional Patent Application No. 62/050,668, filed Sep. 15, 2014. The foregoing applications are fully incorporated herein by reference in their entireties for all purposes.

BACKGROUND

Field of the Invention

The disclosure generally relates to the field of treatment for viral infection and disease using levocetirizine and montelukast.

Description of the Related Art

Several viruses are currently the focus of attention due to their severe acute symptoms and potential for mortality. For instance, Ebola virus elicits a highly lethal hemorrhagic fever for which there are currently no effective vaccines or countermeasures. Ebola also carries a high rate of mortality. West Nile infection, Dengue fever, and yellow fever, caused by mosquito-borne viruses, and tick-borne encephalitis ("TBE"), a tick borne disease caused by the tick borne-encephalitis virus, cause debilitating and long lasting symptoms and, in some instances, also lead to mortality. Each of these viral infections carries a risk of prolonged secondary issues resulting from the acute phase of the viral infection. Malaria, a parasitic infection, also mosquito-borne, also causes debilitating and long lasting symptoms and, in some instances, leads to mortality. This parasitic infection carries a risk of prolonged secondary issues resulting from the acute phase of the infection.

Alzheimer's disease, dementia, dementia with Lewy bodies, Parkinson's, Amyotrophic lateral sclerosis (ALS), frontotemporal dementia, and Huntington's disease are debilitating progressive neurological diseases and disease states. These diseases and disease states currently are inadequately treated.

SUMMARY

Some embodiments described herein pertain to a method of treating a patient having an inflammation-mediated condition. In some embodiments, the method comprises administering to a patient an effective amount of a combination of levocetirizine and montelukast.

Some embodiments described herein pertain to a method of treating a patient having an NFκB-mediated condition. In some embodiments, the method comprises administering to the patient an effective amount of a combination of levocetirizine and montelukast.

Any of the embodiments described above, or described elsewhere herein, can include one or more of the following features or steps. In some embodiments, the condition is a neurological disease.

In some embodiments, the condition treated by administering an effective amount of montelukast and levocetirizine is a condition selected from the group consisting of Alzheimer's disease, dementia, dementia with Lewy bodies, Parkinson's, Amyotrophic lateral sclerosis, frontotemporal dementia, and Huntington's disease. In some embodiments, the condition is one that is caused by a viral infection. In some embodiments, the condition is caused by a virus selected from the group consisting of the Ebola virus, the West Nile virus, the Dengue virus, the tick borne-encephalitis virus, and HIV. In some embodiments, the condition is caused by a parasitic infection. In some embodiments, the parasitic infection is caused by Malaria.

In some embodiments, the combination of levocetirizine and montelukast is administered in a sequential manner. In some embodiments, the combination of levocetirizine and montelukast is administered in a substantially simultaneous manner. In some embodiments, the combination of levocetirizine and montelukast is administered to the patient by one or more of the routes consisting of enteral, intravenous, intraperitoneal, inhalation, intramuscular, subcutaneous and oral. In some embodiments, the levocetirizine and montelukast are administered by the same route. In some embodiments, the levocetirizine and montelukast are administered via different routes. In some embodiments, one or more of levocetirizine or montelukast are provided as a slow release composition.

In some embodiments, the combination further comprises other medications known for use in treating one of the listed conditions. In some embodiments, the combination further comprises a steroid.

Some embodiments pertain to methods of treating a patient having a condition selected from the group consisting of Alzheimer's disease, dementia, dementia with Lewy bodies, Parkinson's, Amyotrophic lateral sclerosis, frontotemporal dementia, and Huntington's disease. In some embodiments, the method comprises administering to the patient an effective amount of a combination of levocetirizine and montelukast.

Some embodiments pertain to methods of treating a patient having a condition selected from the group consisting of Ebola virus, West Nile virus, Dengue virus, tick-borne-encephalitis (TBE), and HIV. Some embodiments pertain to methods of treating a patient having Malaria. In some embodiments, the method comprises administering to the patient an effective amount of a combination of levocetirizine and montelukast.

Some embodiments pertain to methods of treating a patient having an inflammation-mediated condition. In some embodiments, the method comprises identifying a patient with an inflammation-mediated condition. In some embodiments, the method comprises administering to the patient an effective amount of a combination of levocetirizine and montelukast.

Some embodiments pertain to a combination of levocetirizine and montelukast for use in the treatment of an inflammation-mediated condition.

Some embodiments pertain to a combination of levocetirizine and montelukast for use in the treatment of a viral infection. In some embodiments, the viral infection selected from Ebola virus, West Nile virus, Dengue virus, tick-borne encephalitis (TBE), or HIV. Some embodiments pertain to a combination of levocetirizine and montelukast for use in the treatment of a parasitic infection. Some embodiments pertain to a combination of levocetirizine and montelukast for use in the treatment of Malaria.

Some embodiments pertain to a combination of levocetirizine and montelukast for use in the treatment of a neurodegenerative disease. In some embodiments, the neurodegenerative disease is selected from Alzheimer's disease, dementia, dementia with Lewy bodies, Parkinson's, Amyotrophic lateral sclerosis, frontotemporal dementia or Huntington's disease.

Some embodiments pertain to the use of a combination of levocetirizine and montelukast for the manufacture of a medicament for the treatment of an inflammation-mediated condition, a viral infection or a neurodegenerative disease.

Some embodiments pertain to a method of treating a patient having an NFκB mediated condition is disclosed. In some embodiments, the method comprises administering to the patient an effective amount of a combination of levocetirizine and montelukast.

In some embodiments, a method is disclosed for treating a patient having a condition caused by a virus selected from the group consisting of Ebola virus, West Nile virus, Dengue virus, tick-borne encephalitis virus (TBE), and HIV. In some embodiments, the method comprises administering to the patient an effective amount of a combination of levocetirizine and montelukast.

In some embodiments, a method is disclosed for treating a patient having a condition caused by Malaria. In some embodiments, the method comprises administering to the patient an effective amount of a combination of levocetirizine and montelukast.

In some embodiments, a method is disclosed for treating a patient having a condition selected from the group consisting of Alzheimer's disease, dementia, dementia with Lewy bodies, Parkinson's, Amyotrophic lateral sclerosis, frontotemporal dementia, and Huntington's disease. In some embodiments, the method comprises administering to the patient an effective amount of a combination of levocetirizine and montelukast.

BRIEF DESCRIPTION OF THE DRAWINGS

FIG. 1 is a schematic diagram illustrating an NF-kB mediated pathway utilized by RNA viruses, Ebola and Dengue, in upregulating the inflammatory cascade.

DETAILED DESCRIPTION

Figure 2:
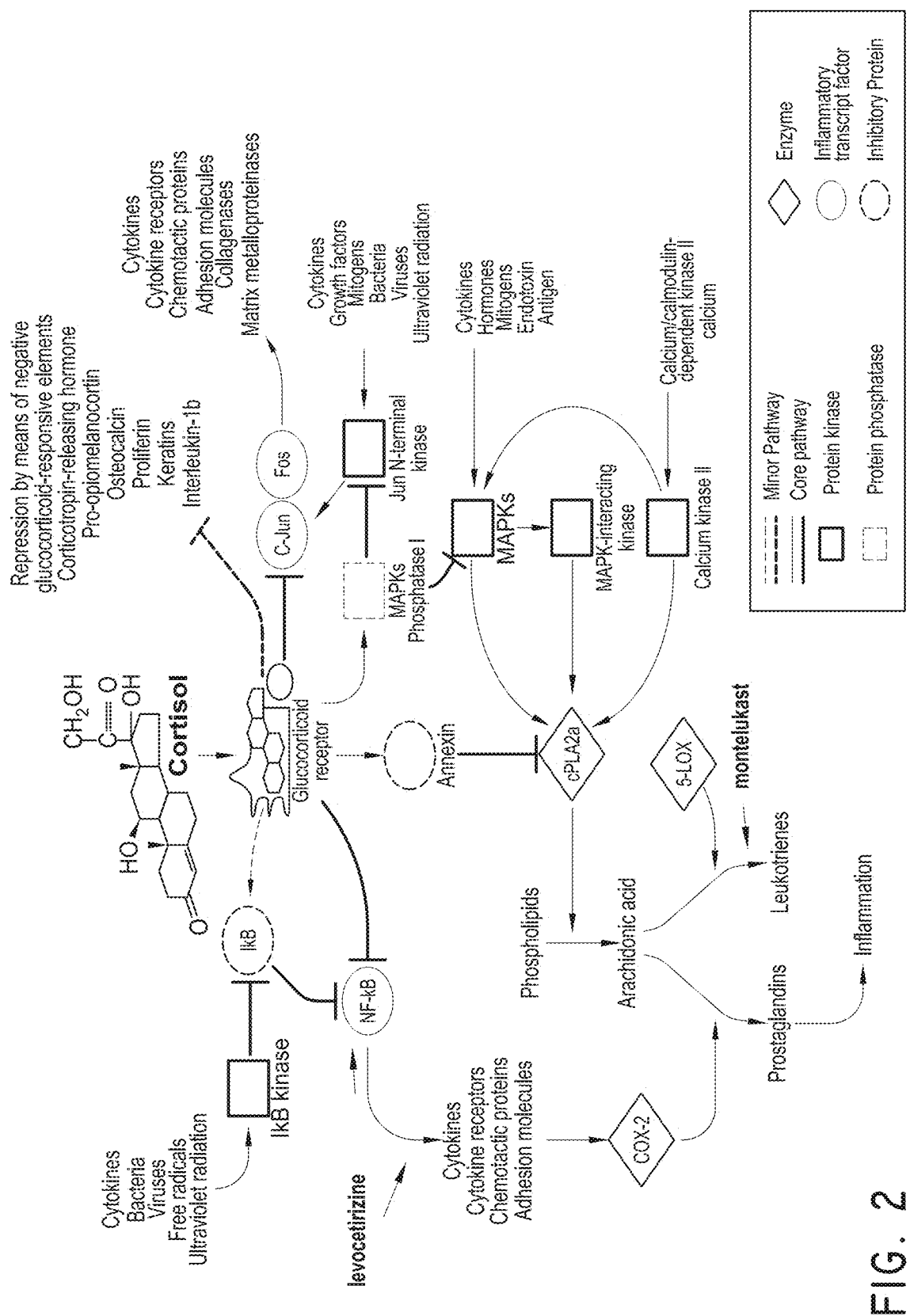
FIG. 2 is a schematic diagram illustrating the actions of levocetirizine and montelukast in treating NF-kB mediated conditions.

Some examples described herein illustrate the use of levocetirizine and montelukast as a medicament for the treatment of viruses and/or diseases. In some embodiments, target viruses and diseases are those that are exacerbated by the inflammatory responses they produce in the body. In some embodiments, by reducing the inflammatory responses they elicit in the body, the viruses and diseases are treated. In some embodiments, the use of a combination of levocetirizine and montelukast targets multiple inflammatory pathways in the body, decreasing inflammation and allowing treatment of viral infection and disease. The examples described herein are illustrative and not intended in any way to restrict the general inventions presented and the various aspects and features of these inventions. Furthermore, the phraseology and terminology used herein is for the purpose of description and should not be regarded as limiting. No features or steps disclosed herein are essential or indispensable.

As used herein, "treatment" pertains to broadly to alleviating the acute and/or long term effects of a virus or disease. Treatment may comprise one or more of slowing progression, shortening duration, decreasing pathogens associated with, alleviating or reducing the symptoms associated with, decreasing the duration of symptoms associated with, and alleviating and/or decreasing long term or residual effects and/or secondary issues associated with viral infection or disease.

Without being bound to any particular theory, it is believed that the combination of levocetirizine and montelukast simultaneously block multiple overlapping and/or separate inflammatory pathways in the body thereby effecting treatment of viruses or diseases (e.g., neurodegenerative disease). It is believed that unchecked, pro-inflammatory reactions divert immune-competent cells in the body, detracting them from their otherwise beneficial anti-pathogenic functions. Exacerbating the problem, and in contrast to clearing the pathogen (e.g., virus or a misfolded protein) or reducing the inflammatory response, the activated cells instead release additional pro-inflammatory mediators diverting immune-competent cells from their roles in immune surveillance. These augmented inflammatory responses contribute to the development and progression of the viral infection or neurodegenerative disease. In some embodiments, levocetirizine and montelukast act by down regulating pro-inflammatory mediators elicited by viruses or diseases allowing the body's own defenses to attack invasive pathogens. In some embodiments, the levocetirizine and montelukast additionally have anti-pathogenic effects that treat viral infections and disease.

In some embodiments, the combination of levocetirizine and montelukast can be used in methods to treat RNA viruses. In some embodiments, the combination of levocetirizine and montelukast is used in a method to treat one or more viruses selected from the group consisting of Ebola virus, West Nile infection, Dengue fever, Yellow Fever, TBE, and HIV. In some embodiments, the methods of treating RNA viruses (or other viruses) with levocetirizine and montelukast achieve synergy by acting on multiple inflammatory signaling pathways in the body. In some embodiments, the combination of levocetirizine and montelukast can be used in methods to treat parasitic infection. In some embodiments, the combination of levocetirizine and montelukast is used in a method to treat Malaria.

In some embodiments, the combination of levocetirizine and montelukast can be used in methods to treat one or more diseases (e.g., neurodegenerative diseases). In some embodiments, the combination of levocetirizine and montelukast are used in methods to treat one or more diseases selected from the group consisting of Alzheimer's disease, Parkinson's disease, multiple sclerosis, Amyotrophic lateral sclerosis, and Huntington's disease. In some embodiments, the combination of levocetirizine and montelukast can be used in methods to treat dementia.

Levocetirizine is an antihistamine and montelukast is a leukotriene receptor antagonist. Levocetirizine, as a potent H1-antihistamine, acts in part by down-regulating the H1 receptor on the surface of mast cells and basophils to block the IgE-mediated release of histamine—the agent responsible for the cardinal symptoms of innate immune responses, including fever, sneezing, rhinorrhea, nasal congestion, itchy palate, and itchy red and watery eyes. Levocetirizine even decreases certain viral titers in vitro by log-2 (e.g., rhinovirus). Montelukast, a leukotriene receptor antagonist, acts by binding with high affinity and selectivity to the CysLT1 receptor to inhibit the physiologic actions of the leukotriene LTD4 (see FIG. 2). Leukotrienes are fatty signaling molecules whose effects include airway edema, smooth muscle contraction and altered cellular activity associated with the inflammatory process. Overproduction of leukotrienes is a significant contributor to inflammation in viral infection and neurodegenerative disease.

Levocetirizine and montelukast are in different drug classes and target different receptors in the body. Whereas they target different receptors in the body, levocetirizine and montelukast can achieve their effect via different molecular pathways. In some embodiments, the combination of montelukast and levocetirizine achieves synergy to shorten the course of viral infection and disease by targeting these different pathways in the body. In some embodiments, multiple inflammatory signaling pathways in the body are targeted to achieve treatment of viral infection or disease with levocetirizine and montelukast. In some embodiments, synergy is achieved by downregulating certain inflammatory processes. In some embodiments, the use of the combination of montelukast and levocetirizine decreases one or more of the symptoms of, the duration of, morbidity from, and mortality from viruses and inflammation-related diseases and viruses. In some embodiments, the combination of levocetirizine and montelukast decreases the rate of virus and/or disease progression. In some embodiments, the combined levocetirizine and montelukast therapy can improve quality of life by ameliorating symptoms/side effects/the viral or disease process itself, resulting in decreased healthcare costs. In some embodiments, a synergistic effect can be observed in the use of a combination of levocetirizine and montelukast to treat inflammation.

Without being bound to any particular theory, the effect of the combination of levocetirizine and montelukast is due, at least in part, to the fact that both levocetirizine and montelukast affect eosinophil migration/quantity; the eosinophil is considered by scientists/clinicians as one hallmark of inflammation. Additionally, as discussed elsewhere herein, the response may be related, at least in part, due to levocetirizine's interference with the toll-like receptors (TLRs) and montelukast's separate interference with the leukotriene-related pathways to inflammation.

In some embodiments, the combination of levocetirizine and montelukast can be used in methods to treat viruses and diseases that activate the immune system via pathogen-associated molecular patterns (PAMPs). PAMPs are molecular structures carried on pathogens and that have been substantially conserved over time. PAMPs comprise glycoproteins, lipopolysaccharides, proteoglycans and nucleic acid motifs broadly shared by microorganisms that are essential to their survival. Because PAMPs have been evolutionarily conserved in nature, the mammalian innate immune system has evolved to recognize them.

Immune recognition of these PAMPs is accomplished using encoded protein pattern recognition receptors (PRRs). PRRs can be activated by pathogens such as viruses (e.g., RNA viruses), at which time they upregulate the transcription of cytokines, chemokines, type I interferons (IFNs), and antimicrobial proteins. This upregulation initiates one or more inflammation cascades that may interfere with the body's ability to defend against viruses. Triggered innate immune mechanisms are also emerging as a crucial component of major neurodegenerative diseases. Microglia and other cell types in the brain can be activated in response to pathogens (e.g., misfolded proteins or aberrantly localized nucleic acids). This diverts microglia from their physiological and beneficial functions, and leads to their sustained release of pro-inflammatory mediators. Activation of innate immune signaling pathways—in particular, the NOD-, LRR- and pyrin domain-containing 3 (NLRP3) inflammasome by aberrant host proteins can lead to the development of diverse neurodegenerative disorders. During chronic activation of microglia, the sustained exposure of neurons to pro-inflammatory mediators can cause neuronal dysfunction and contribute to cell death. Because chronic neuroinflammation is observed at relatively early stages of neurodegenerative disease, targeting the mechanisms that drive this process is useful for therapeutic purposes.

In some embodiments, the combination of levocetirizine and montelukast treats viruses that activate the innate immune system by blocking certain inflammatory responses. In some embodiments, the combination of levocetirizine and montelukast can be used in methods to treat viruses that activate the innate immune system via PRRs and/or that upregulate pro-inflammatory factors including one or more of cytokines, chemokines, and type I interferons (IFNs). In some embodiments, the combination of levocetirizine and montelukast treat viruses that upregulate one or more of cytokines, chemokines, type I interferons (IFNs), and antimicrobial proteins by decreasing inflammation associated with these viruses and/or by blocking upregulation of these pro-inflammatory factors. In some embodiments, the combination of levocetirizine and montelukast treat viruses by down regulating one or more of cytokines, chemokines, and type I interferons (IFNs). In some embodiments, in addition to downregulating the above agents, the combination of levocetirizine and montelukast act by decreasing viral titers.

In some embodiments, the combination of levocetirizine and montelukast treats pathogens (e.g., misfolded proteins) that contribute to inflammation-related diseases (e.g., neurodegenerative diseases) that activate the innate immune system. In some embodiments, the combination of levocetirizine and montelukast treat neurodegenerative disease by blocking certain inflammatory responses. In some embodiments, the combination of levocetirizine and montelukast can be used in methods to treat diseases that progress through prolonged activation of the immune system (e.g., the adaptive as well as the innate immune system) via PRRs. In some embodiments, the combination of levocetirizine and montelukast treat neurodegenerative diseases by preventing the upregulation of one or more of cytokines, chemokines, and type I interferons (IFNs) and by decreasing inflammation associated with these factors. In some embodiments, the combination of levocetirizine and montelukast down regulate one or more of cytokines, chemokines, and type I interferons (IFNs) to treat neurodegenerative disease. In some embodiments, in addition to downregulating the above agents, the combination of levocetirizine and montelukast contributes to a decrease in pathogens associated with neurodegenerative disease.

Toll-like receptors (TLRs) are a particular type of PRR that have substantial importance in the initiation of antiviral response upon infection. In some embodiments, the combination of levocetirizine and montelukast can be used in methods to treat viruses and/or disease by interfering with the innate immune system signaling pathways that operate, at least in part, through TLRs. In some embodiments, the combination of levocetirizine and montelukast treats viruses, such as RNA viruses, and neurodegenerative diseases that activate innate immune receptors (such as RNA viruses or neurodegenerative diseases). In some embodiments, the combination of levocetirizine and montelukast treats viruses and diseases that activate immune responses via TLRs by interfering with TLR activation.

TLRs comprise of family with 10 members in humans (TLR1, TLR2, etc.). TLR2, TLR3, TLR4, TLR7 and TLR8 are of importance in recognizing structural features of RNA viruses—both double-stranded and single-stranded—as well as surface glycoproteins. Table 1 below demonstrates some viral targets of TLRs for which the combination of levocetirizine and montelukast are effective in treating:

TABLE 1

Individual TLRs and the RNA viruses recognized by them.

| Receptor | Virus | Ligand |
|---|---|---|
| TLR7 | Influenza A virus | ssRNA |
| | Vesicular stomatitis virus | ssRNA |
| | Human immunodeficiency virus | ssRNA |
| | Dengue virus | ssRNA |
| | Sendai virus | ssRNA |
| | Lactate dehydrogenase-elevating virus | ssRNA |
| | Mouse mammary tumor virus | ssRNA |
| | Murine leukemia virus | ssRNA |
| TLR8 | Human immunodeficiency virus | ssRNA |
| TLR3 | Reoviridae | dsRNA |
| | Respiratory syncytial virus | dsRNA |
| | West Nile virus | dsRNA |
| | Coxsackievirus B3 | dsRNA |
| | Poliovirus | dsRNA |
| | Influenza A virus | dsRNA |
| | Punta Toro virus | dsRNA |
| TLR2 | Measles virus | HA |
| | Lymphocytic choriomeningitis virus | ? |
| | Hepatitis C virus | Core protein/NS3 |
| TLR4 | Respiratory syncytial virus | Fusion protein |
| | Coxsackievirus B4 | ? |
| | Mouse mammary tumor virus | Envelope protein |
| | Murine leukemia virus | Envelope protein |

The TLR family is also involved in the recognition a broad range of RNA viruses as well as non-RNA viruses, fungi, parasites, and bacteria. In some embodiments, the combination of levocetirizine and montelukast treats inflammation-related disease where inflammation is propagated via TLRs. In some embodiments, the combination of levocetirizine and montelukast is used in methods to treat inflammation-related disease or viral infection by down regulating inflammation activated at least in part through receptors consisting of the group consisting of TLR7, TLR8, TLR3, TLR2, TLR4, and combinations thereof.

A common feature of all TLR recognition is the activation of three major signaling pathways: nuclear factor kappa-light-chain-enhancer of activated B cells (NF-kB), mitogen-activated protein kinase (MAPKs), and one or more of the interferon regulatory factors (IRFs). In some embodiments, the combination of levocetirizine and montelukast is used in methods to treat viruses and/or inflammation-related disease by blocking activation of one or more of these pathways.

NF-kB plays a pivotal role across a spectrum of inflammation, immunity, cell proliferation, differentiation, and survival. In some embodiments, the combination of levocetirizine and montelukast is used in methods to treat viruses and diseases that elicit cellular activity or inflammatory responses via NF-kB. In some embodiments, the combination of levocetirizine and montelukast treats viruses and/or inflammation-related disease by blocking activation through the NF-kB pathway. In some embodiments, the combination of levocetirizine and montelukast treats viruses and/or inflammation-related disease by blocking TLR activation through the NF-kB pathway and at least one other cellular signaling pathway selected from the group consisting of the MAPKs pathway and the IRFs pathway. In some embodiments, the combination of levocetirizine and montelukast treats viruses and/or inflammation-related disease by blocking cellular signaling pathways other than those mediated by TLRs.

MAPKs active activator protein 1, together with NF-kB, induces the expression of genes required for inflammatory responses (and for adaptive immune responses) including IL-1β, IL-6, IL-18, and tumor necrosis factor (TNF). In some embodiments, the combination of levocetirizine and montelukast are used in methods to treats viruses and disease in part through blocking activation of MAPK pathways. In some embodiments, the combination of levocetirizine and montelukast treats viruses and disease by blocking or inhibiting the expression of one or more of IL-1β, IL-6, IL-18, and tumor necrosis factor (TNF).

IFNs also play a central role in the induction of antiviral responses and trigger transcription of IFN-inducible genes that influence protein synthesis, growth regulation, apoptosis, maturation of dendritic cells, cytotoxicity of natural killer cells, and differentiation of virus-specific cytotoxic T lymphocytes. IFNs are also linked to inflammatory responses related to viral infection and disease. In some embodiments, the combination of levocetirizine and montelukast treats viruses and/or inflammation-related disease in part through blocking activation of IRF and/or IFN pathways. IRF3 and IRF7 are essential for the induction of the type I interferons (IFN). In some embodiments, the combination of levocetirizine and montelukast treats viruses and/or inflammation-related disease in part through blocking activation of one or more of IRF3 and IRF7.

Retinoic acid-inducible gene I (RIG-I) like receptors (RLRs) are cytosolic protein sensors expressed by most cells of the human organism. RLRs are critical sensors of viral infection in most cell types. Upon binding to viral RNA structures produced during viral replication, two repeats of a cysteine-aspartic protease (caspase)-recruiting domain (CARD)-like region at the N terminus are exposed. These then interact with other CARD containing proteins to trigger downstream signaling events. RLRs are typically found in low concentrations in the cell, but, once a virus is detected, they are upregulated in much greater concentrations. In some embodiments, the combination of levocetirizine and montelukast is used in methods to down regulate activation of RLRs. In some embodiments, the combination of levocetirizine and montelukast are used in methods to treat viruses in part by down regulating the activation of RLRs.

RIG-I, as an RLR, is important in recognizing and initiating cytokine production in response to a wide range of viruses from many different families. These families include the Ebola Virus. Recognition is antagonized by the Ebola virus V35 protein, as the secreted V35 binds the dsRNA ligand preventing the activation of RIG-1 mediated signaling. Table 2, below, shows several RNA virus targets of RIG-I.

TABLE 2

Individual RLRs and the RNA viruses recognized by them

| Receptor | Virus | Ligand |
|---|---|---|
| RIG-I | Sendai virus | ss/dsRNA |
| | Newcastle disease virus | ss/dsRNA |
| | Respiratory syncytial virus | ss/dsRNA |
| | Measles virus | ss/dsRNA |
| | Nipah virus | ss/dsRNA |
| | Vesicular stomatitis virus | ss/dsRNA |
| | Rabies virus | ss/dsRNA |
| | Influenza A virus | ss/dsRNA |
| | Influenza B virus | ss/dsRNA |
| | Ebola virus | ss/dsRNA |

TABLE 2-continued

Individual RLRs and the RNA viruses recognized by them

| Receptor | Virus | Ligand |
|---|---|---|
| | Lassa virus | ss/dsRNA |
| | Lymphocytic choriomeningitis virus | ss/dsRNA |
| | Rift Valley fever virus | ss/dsRNA |
| | Japanese encephalitis virus | ss/dsRNA |
| | Hepatitis C virus | ss/dsRNA |
| | West Nile virus | ss/dsRNA |
| | Dengue virus | ss/dsRNA |
| | Rotavirus | ss/dsRNA |
| MDA5 | Encephalomyocarditis virus | dsRNA |
| | Theiler's virus | dsRNA |
| | Mengo virus | dsRNA |
| | Rabies virus | dsRNA |
| | West Nile virus | dsRNA |
| | Sendai virus | dsRNA |
| | Dengue virus | dsRNA |
| | Rotavirus | dsRNA |
| | Murine hepatitis virus | dsRNA |
| | Murine norovirus 1 | dsRNA |

In some embodiments, the combination of levocetirizine and montelukast is used in methods of blocking activation of inflammation via the RIG-I pathway. In some embodiments, the combination of levocetirizine and montelukast treats viruses (and/or neurological disease) by blocking activation of the RIG-I pathway.

Melanoma differentiation-associated antigen 5 (MDA5) is structurally similar to RIG-I. It initiates cytokine and type I IFN production via IPS-1 similarly to RIG-I and is important in initiating cytokine responses to picornaviruses, including encephalomyocarditis virus, Theiler's virus, and Mengo virus. MDA5 is important in antiviral activation against Sendai virus and works cooperatively with RIG-I to respond to West Nile virus, rabies virus, Dengue virus, and rotavirus. Table 2 contains a list of known viral targets of RIG-I and MDA5. In some embodiments, the combination of levocetirizine and montelukast is used in methods of downregulated MDA-5 activation. In some embodiments, the combination of levocetirizine and montelukast is used in methods of treating viruses and/or inflammation-related disease by downregulating activation of inflammatory responses through the MDA-5 pathway. In some embodiments, the above methods are accomplished using a sustained release formulation. In some embodiments, the sustained release formulation targets the NF-kB pathway.

Laboratory of genetics and physiology 2 (LGP2) is another RLR. The LGP2 gene lacks the region encoding CARD in RIG-I and MDA5. Since this region is responsible for association with IPS-1 and therefore further signaling events, LGP2 is thought to be a negative regulator of RLR signaling via interaction between the RD of LGP2 and that of RIG-I. LGP2 is assumed to be a modulator of the innate immune response to a viral infection and not a sensor of PAMPs in that LGP2 does not initiate antiviral gene expression. LGP2 may mediate the modulator role by inhibiting RIG-I signaling via competitive interaction with viral dsRNA species in one scenario, while in another, enhancing the ability of MDA5 to sense long dsRNA structures by complexing with MDA5. In some embodiments, the combination of levocetirizine and montelukast is used in methods to treat viruses and/or inflammation-related disease that elicit inflammation by upregulating the LGP2 pathway. In some embodiments, the combination of levocetirizine and montelukast is used in methods to treat viruses and/or inflammation-related disease by interfering with the LGP2 pathway.

Interferon promoter stimulator 1 (IPS-1) is located at the cytosolic face of the outer mitochondrial membrane, and this mitochondrial association is initiates further signaling events. Both RIG-I and MDA5 interact with the adaptor IPS-1 through CARD repeats. IPS-1-deficient mice are impaired in the production of proinflammatory cytokines and type I IFN in response to all RNA viruses recognized by RIG-I and MDA5, indicating a key role of IPS-1 in downstream signaling from RIG-I and MDA5. While IPS-1 itself is probably not directly involved in the signaling process it likely serves plays a role in orchestrating the activation of IRF3 and NF-kB. In some embodiments, the combination of levocetirizine and montelukast is used in methods of downregulated IPS mediated activation of IRF3 and NF-kB pathways. In some embodiments, the combination of levocetirizine and montelukast is used in methods of treating viruses and/or inflammation-related disease by downregulating activation of inflammatory responses through IPS mediated activation of IRF3 and NF-kB pathways.

Another stimulator of IFN genes, called STING (also called MITA) and found in the mitochondrial membrane, interacts with RIG-I and IPS-1 in the mitochondrial membrane—potentially initiating communication between organelles in viral sensing. Given that some viruses replicate in the membranes of organelles, the STING stimulator is a target for interfering with viral-based inflammation and/or replication. In some embodiments, the combination of levocetirizine and montelukast treats viruses and/or inflammatory related disease by interfering with the STING stimulator.

Figure 1:
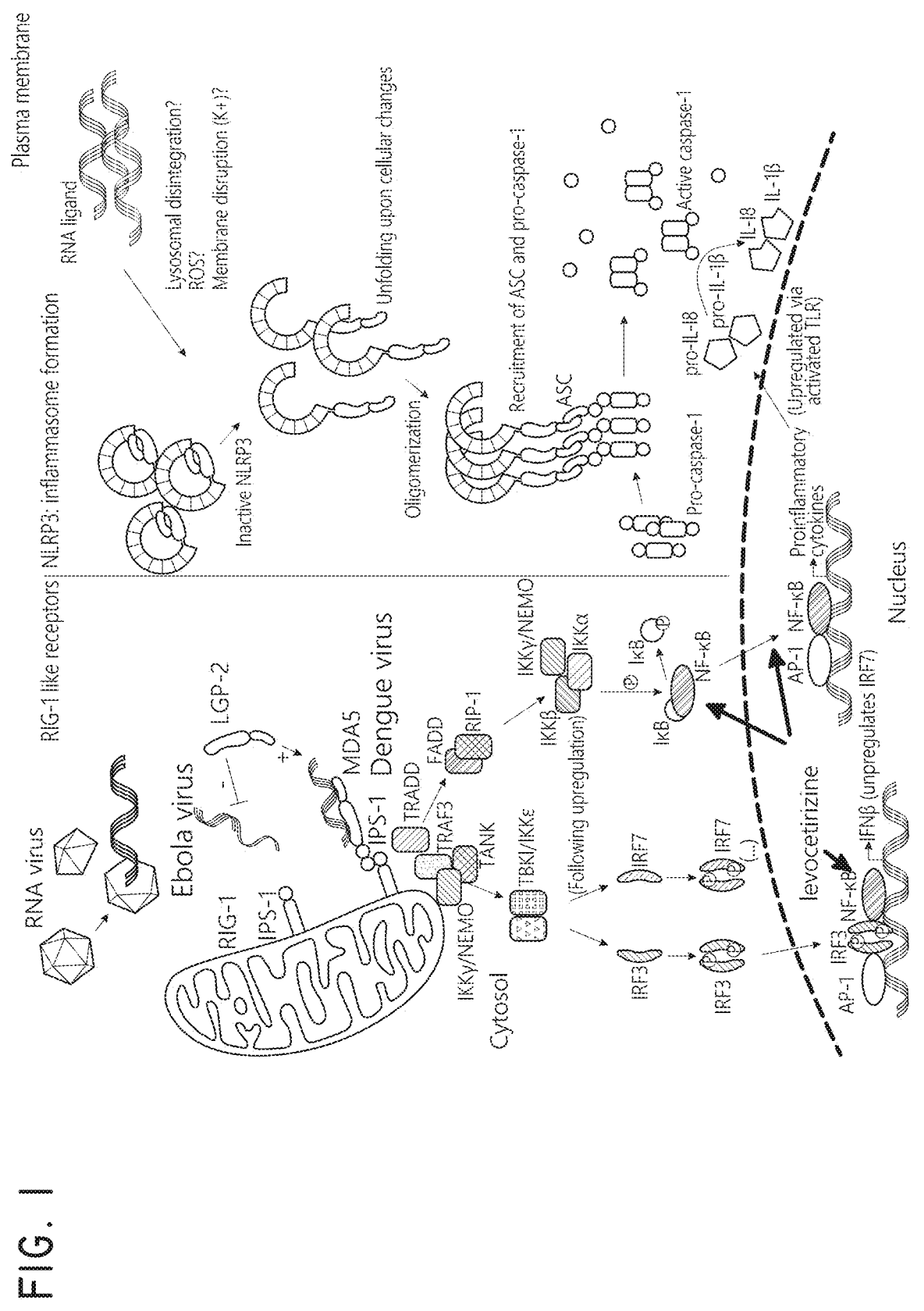

IPS-1 coordinates the activation of two pathways which leads to NF-kB nuclear translocation and the activation of inhibitors of NF-kB kinase (IKK) (see FIG. 1). Central in the initiation of both pathways is the TNF receptor-associated death domain (TRADD), which is recruited to IPS-1 and coordinates interactions with downstream molecules. The IPS-1/TRADD complex recruits TRAF3, which together with TANK and IKK/NEMO initiates the activation of IKKs. Similarly, this complex recruits receptor interacting protein 1 (RIP1) (in a complex with the Fas-associated death domain [FADD]) for the initiation of the NF-KB pathway. In some embodiments, the combination of levocetirizine and montelukast treats viral infection or disease at least in part by interfering with these pathways. As shown in FIG. 1, this interference may specifically target the NF-kB receptor.

Not to be bound by a particular theory, in some embodiments, the cellular mechanism of action is proposed to be at least in part a reduction of the activation of the intracellular protein complex NF-kB (nuclear factor kappa B) which is in turn responsible for the reduction of certain transmembrane proteins (e.g., I-CAM-1). I-CAM-1, a transmembrane protein, is viewed as the portal of entry of some viruses into the cell (e.g., rhinovirus). Rhinovirus can be found in ~50% of cases of acute asthma and is responsible for 30-50% cases of the "common cold." A one-log reduction in viral titers has been independently determined to correlate with improved symptoms. In addition, levocetirizine has been shown to decrease eosinophil migration/quantity and decrease inflammatory mediators, IL-4, IL-6, and IL-8. IL-6, a signaling protein, regulates in part: fever, the body's response to trauma, and the acute (immediate) phase of an immune response. It is believed that these same effects through modulation the innate/adaptive immune system, may reduce viral titers of one or more of the Ebola virus, the Dengue virus, the West Nile virus, the Yellow fever virus, and the TBE virus. It is also believed that these effects through modulation the innate/adaptive immune system may reduce parasite levels in, for example, Malaria. Parasitic disease is classically associated with an eosinophilic response. Regarding montelukast, the cysteinyl leukotrienes (e.g., LTC4, LTD4, LDE4, etc.) are products of arachidonic acid metabolism. These leukotrienes are released from various cells including mast cells and eosinophils. They bind to receptors in the human airway and on other pro-inflammatory cells including eosinophils and certain myeloid stem cells. The cysteinyl leukotrienes have been correlated with the pathophysiology of asthma and allergic rhinitis. In some embodiments, the combination of levocetirizine and montelukast treats viral infection of disease at least in part by interfering with these pathways, ligands, and/or receptors.

Without being bound by any particular theory, it is believed that as RLR (RIG-I-like receptor) signaling converges on pathways also utilized by the TLRs, the induced gene expression is also similar, leading to synthesis and release of type I IFN s and proinflammatory cytokines in order to launch an antiviral inflammatory response. RLR signaling is modified by ubiquitination, direct protein interactions, and caspase activity in an elaborate network of both positive and negative regulation. In some embodiments, the combination of levocetirizine and montelukast treats viral infection or disease at least in part by interacting with these pathways.

In addition to the signaling pathway described above, RIG-I activation may trigger inflammasome formation and cysteine-aspartic protease 1 (caspase-1) activity, leading to the maturation of proinflammatory cytokines such as interleukin-1β (IL-1β). This IPS-1-independent pathway is also used by NLRP3. NLRs or NOD-like receptors (nucleotide-binding oligomerization domain-containing) are cytosolic proteins regulating the inflammatory and apoptotic responses (NLRP3, NLRC2, and NLRC5). These receptors are additionally important in antiviral defense. In some embodiments, the combination of levocetirizine and montelukast treats viral infection or disease at least in part through interaction with one or more of these pathways or ligands.

NLRP3, NOD-like receptor family, pyrin domain-containing 3, presumably through lysosomal degeneration and membrane disruption ultimately mediates the formation of fully functional IL-1β and IL-18. The specific stimuli initiating aggregation of the NLRP3 inflammasome are still unresolved. It shares a common pathway with NF-kB and is likely an indirect sensor of viral invasion. (Table 3, FIG. 1).

TABLE 3

Individual NLRs and the RNA viruses recognized by them

| Receptor | Virus | Ligand |
|---|---|---|
| NLRP3 | Influenza A virus | Virus→cell stress? |
|  | Sendai virus | Virus→cell stress? |
| NLRC2 | Respiratory syncytial virus | ssRNA |
|  | Influenza A virus | ssRNA |
|  | Parainfluenza virus | ssRNA |

FIG. 1 also shows the RIG-1 and NLRP3 signaling pathway. In some embodiments, the combination of levocetirizine and montelukast treats viral infection of disease at least in part through interaction with these pathways.

In some embodiments, combined levocetirizine and montelukast therapy decreases, in part, upregulation of ICAM-1 and IL-6. ICAM-1, in the established pathway to leucocyte extravasation, is a significant biomarker for hemorrhage. IL-6 is a significant biomarker for fatality. Ebola is a highly virulent pathogen which operates in part through the ICAM-1 and IL-6 pathways. The Ebola virus genus includes five different viruses: Sudan virus (SUDV), Tai Forest virus (TAFV), Reston virus (RESTV), Ebola virus (EBOV), and Bundibugyo virus (BDBV). Ebola has the highest fatality rate (25-90%) followed by Sudan virus and has the present risk of becoming endemic in Africa. In some embodiments, the combination of levocetirizine and montelukast are effective for treating one or more of Sudan virus (SUDV), Tai Forest virus (TAFV), Reston virus (RESTV), Ebola virus (EBOV), and Bundibugyo virus (BDBV).

The incubation period of Ebola virus is between 2-21 [World Health Organization] days followed by the onset of headache, fever, extreme fatigue, and gastrointestinal distress. Initial principal viral targets are the dendritic cells (DCs), vascular monocytes, and tissue macrophages. Infection of the monocytes and macrophages leads to a massive release of pro-inflammatory cytokines and chemokines. This "cytokine storm" recruits additional antigen presenting cells to the site of infection to escalate the process.

Altered chemistries include, but are not limited to, an elevated AST (aspartate aminotransferase—liver enzyme), D-dimer, blood urea nitrogen, and creatinine. Serum calcium and albumin are lower in fatal cases. Elevated signaling proteins include in part, IL-6, IL-8, Il-10, and macrophage inflammatory protein 1β (MIP-1β). A rise in an acute phase signaling protein, IL-6, and ICAM-1 (Intracellular adhesion molecule-1), have been correlated with death and hemorrhage, respectively. In some embodiments, the combination of levocetirizine and montelukast treats these viral infections at least in part through interaction with these pathways.

Clinically, bleeding, petechiae (small hemorrhages) and a maculopapular rash frequently occur between 2 and 7 days. Death can follow and is underscored by massive tissue injury and multi-organ system failure characterized by vascular permeability, dissemination intravascular permeability and hemorrhage. It is commonly held that the abatement of the coagulopathy in both Ebola and sepsis improves survival outcomes. The clinical response to existing therapy has been limited by multiple strategies through which the virus antagonizes the INF-α and INF-β response. Terminal stages of Ebola are underscored by a dysregulated inflammatory response resulting in vascular permeability, dissemination intravascular coagulation and multiorgan system failure. In some embodiments, the combination of levocetirizine and montelukast alleviates or decreases one or more of bleeding, petechiae (small hemorrhages), a maculopapular rash, massive tissue injury, multi-organ system failure characterized by vascular permeability, and death associated with Ebola infection.

The Ebola virus as a highly virulent organism has evolved to sustain itself through different pathways. First, two structural proteins, viral protein 24 (VP24) and viral protein 35 (VP35) act in concert to desensitize hosts cells to the effects of IFN-α/β and IFN-γ. Second, the EBOV glycoprotein (GP) facilitates budding from infected cells and participates in epitope masking and steric shielding. The resulting dense concentration of glycans creates a difficult environment for the binding of neutralizing antibodies. The glycan barrier contributes to the pathogenesis. In some embodiments, the combination of levocetirizine and montelukast treats viral infection at least in part through interaction with one or more of these pathways or ligands.

In general RIG-1 is activated by viral RNA to induce a type I IFN responses to control viral replication. A cellular dsRNA binding protein called PACT can also activate RIG-1. Recent science appears to support the concept that a mutual antagonism between the Ebola virus VP35 protein and RIG-1 activator PACT determines the infection outcome. That being said, although PACT interacts with the C terminus of RIG-1, the structural and biochemical basis by which it modulates RIG-1 activation remains incompletely understood.

Ebola as a highly pathogenic organism will more likely than not require sustained tissue levels to decrease morbidity and mortality (25-90%). Initial flu-like symptoms rapidly progress to severe nausea, diarrhea, shortness of breath, hypotension, bleeding and coma. The current focus of therapy for the Ebola virus is supportive. Traditional measures, assuming such basics are available in medically underserved regions, include intravenous fluid for hydration and maintenance of electrolyte balance, insulin for regulation of glucose, supplemental oxygen when necessary to provide adequate tissue saturation, analgesics for pain, headache, and myalgia, and prophylactic antibiotics to treat secondary opportunistic bacterial infections.

The use of platelet transfusions and fresh frozen plasma are the standard of care for the treatment of DIC (disseminated intravascular coagulation). Heparin may be of value in patients with low-grade DIC; however, there are no controlled clinical trials. Therapeutic intervention focusing on coagulopathy in nonhuman models of EBOV (Recombinant human activated protein C, Recombinant inhibitor of factor VIIa/tissue factor) have only moderately increased survival. Recently the use of statins have been suggested to decrease inflammation and potentially improve survival; however, IV forms of these medications have not been developed.

West Nile virus is an infectious virus transmitted by mosquitos. Like for Ebola, there are currently no vaccines for West Nile Virus. Symptoms of West Nile infection (when present) typically occur between 2 and 15 days after infection and may include one or more of the following: fever, headache, fatigue, muscle pain or aches (myalgia), malaise, nausea, anorexia, vomiting, and rash. In some patients, neurological diseases can occur. Those more susceptible to major symptoms of West Nile virus are the elderly, the very young, or those with immunosuppression (e.g., medically induced, such as those taking immunosuppressive drugs, or medically compromised due to a pre-existing medical condition such as HIV infection). Neurological diseases associated with West Nile virus encephalitis, which causes inflammation of the brain, West Nile meningitis, which causes inflammation of the meninges, which are the protective membranes that cover the brain and spinal cord, West Nile meningoencephalitis, which causes inflammation of the brain and also the meninges surrounding it, and West Nile poliomyelitis—spinal cord inflammation, which results in a syndrome similar to polio, which may cause acute flaccid paralysis.

Like Ebola and West Nile, there are also currently no vaccines for the Dengue virus. In Dengue fever (caused by the Dengue virus) symptoms typically occur from about 3 to 14 days after exposure to the virus. Symptoms (where present) can include fever, headache (typically located behind the eyes), muscle and joint pains, rash, nausea, vomiting, bleeding from the mucous membranes of the mouth and nose, leakage of plasma from the blood vessels (resulting in fluid build-up in the abdomen, loss of circulation and organ dysfunction), dengue shock syndrome, and hemorrhagic fever.

Yellow Fever is another potentially fatal infectious virus. Unlike Ebola, West Nile, and Dengue virus, a vaccine to Yellow fever exists. Yellow Fever symptoms typically occur approximately 3 to 6 days after exposure to the yellow fever virus. Most cases only cause a mild infection with fever, headache, chills, back pain, fatigue, loss of appetite, muscle pain, nausea, and vomiting. In about 15% of cases, however, people enter a toxic phase of the disease with recurring fever, accompanied by jaundice due to liver damage, abdominal pain, and bleeding in the mouth, the eyes, and the gastrointestinal tract (which causes vomit to contain blood). This toxic phase is fatal in about 20% of cases, making the overall fatality rate of the disease about 3%. In severe epidemics mortality may exceed 50%

Tick-Borne Encephalitis (TBE) is caused by the TBE virus which has three subtypes: (a) European or Western TBC, (b) Siberian TBE, and (c) Far Eastern TBE. TBE can infect the brain (encephalitis), the meninges (meningitis) or both (meningoencephalitis) resulting in a 1% to 2% mortality rate; generally about 5 to 7 days after the onset of neurologic symptoms.

Each of the Ebola virus, the Dengue virus, the West Nile virus, the Yellow fever virus, and the TBE virus, have common inflammatory pathways shown above. Clinically effective therapy for a high virulent organism (such as one or more of the Ebola virus, the Dengue virus, the West Nile virus, the Yellow fever virus, and the TBE virus) requires a multifaceted approach to more than one target within the inflammatory cascade. Using the steroid pathway (FIG. 2) as an accepted and time-proven clinical model, levocetirizine acts not only at the H1-receptor but also at the level of NF-kB (see FIG. 1). Simultaneously montelukast functions at the $LTD_4$ receptor to synergistically decrease inflammation. In some embodiments, the combination of levocetirizine and montelukast treats one or more of these viruses by acting on multiple pathways. In some embodiments, the combination of levocetirizine and montelukast provides a synergistic effect by disrupting different inflammatory pathways simultaneously. In some embodiments, the combination of levocetirizine and montelukast is used in methods of treating any of the viruses listed in any one of Tables 1-3. In some embodiments, the combination of levocetirizine and montelukast is used in methods of treating any of the viruses listed in any one of Tables 1-3 through the synergistic activities of levocetirizine through one of the above named pathways and through montelukast's activity through an alternative pathway.

Malaria is a mosquito-borne parasite. Signs and symptoms of malaria typically begin 8-25 days following infection; however, symptoms may occur later in those who have taken antimalarial medications as prevention. Initial manifestations of the disease—common to all malaria species—are similar to flu-like symptoms, and can include headache, fever, shivering, joint pain, vomiting, hemolytic anemia, jaundice, hemoglobin in the urine, retinal damage, and convulsions. The classic symptom of malaria is paroxysm—a cyclical occurrence of sudden coldness followed by shivering and then fever and sweating, occurring every two days (tertian fever) in P. vivax and P. ovale infections, and every three days (quartan fever) for P. malariae. P. falciparum infection can cause recurrent fever every 36-48 hours, or a less pronounced and almost continuous fever. Severe malaria is usually caused by P. falciparum (often referred to as falciparum malaria). Symptoms of falciparum malaria arise 9-30 days after infection. Individuals with cerebral malaria frequently exhibit neurological symptoms, including abnormal posturing, nystagmus, conjugate gaze palsy (failure of the eyes to turn together in the same direction), opisthotonus, seizures, or coma.

Malaria and other parasitic infections also operate though some of the inflammatory pathways shown above. In some embodiments, the combination of levocetirizine and montelukast treats one or more parasites by acting on multiple inflammation pathways. In some embodiments, the combination of levocetirizine and montelukast provides a synergistic effect by disrupting different inflammatory pathways simultaneously to treat Malaria.

Some embodiments provide the combination of levocetirizine and montelukast as a medicament for the treatment of viruses and diseases that activate innate immune responses or that are exacerbated and/or caused by immune responses (e.g., the adaptive immune response). In some embodiments, the combination of levocetirizine and montelukast treats viruses and/or diseases that activate innate immune responses at least in part via Toll-Like Receptors (TLRs). In some embodiments, the combination of levocetirizine and montelukast reduces the activation of one or more elements of the NF-kB family of transcription factors (NF-kB: nuclear factor kappa B) resulting in a therapeutic effect. In some embodiments, the combination of levocetirizine and montelukast reduces the activation of the NF-kB/toll-like receptors and/or other intracellular or extracellular protein complexes (e.g., exosomes, histones). In some embodiments, the combination of levocetirizine and montelukast treats viruses or other diseases that are activated at least in part through NF-kB. Without being bound to a particular theory, delivery of levocetirizine and montelukast (e.g., sustained, intermittent, or otherwise) will stabilize NF-kB through the overexpression of the H1-receptor in a dose-dependent manner.

As discussed above, innate immune activation also plays a role in neurodegenerative disease. In neurodegenerative diseases, microglia cells are exposed to activated by pathogens through the triggering of PRRs, including TLR2, TLR4, and TLR6. In addition to these receptors, some TLR ligands also engage co-receptors such as CD36 (also known as platelet glycoprotein 4), CD14 and CD47. The activation of TLRs and their co-receptors by danger-associated molecular patterns (DAMPs) and PAMPs initiates an immune response. As there is a strong overlap between the signaling pathways that are induced by PAMPs and DAMPs, microglia may not be able to discriminate between invading pathogens and misfolded or aberrant endogenous molecular patterns. Various self molecules that are present in degenerating brains can activate immune receptors—for example, aggregated amyloid-β and α-synuclein, mutant huntingtin (HTT), mutant superoxide dismutase 1 (SOD1), the S1OOA9-S1OOA8 complex (also known as MRP14-MRP8) and chromogranin A. In some embodiments, the combination of levocetirizine and montelukast treat neurodegenerative disease by targeting one or more of these receptors or by blocking one or more of these ligands from inducing inflammatory activity.

A common feature of neurodegenerative diseases is the excessive production and release of pro-inflammatory cytokines of the interleukin-1β (IL-1β) family, including IL-1β and IL-18. Inflammasomes consist of a sensor molecule from the NOD-like receptor (NLR) family or the pyrin and HIN domain-containing protein (PYHIN) family, the adaptor protein ASC and caspase 1. The NOD-, LRR- and pyrin domain-containing 3 (NLRP3) inflammasome is of particular importance in the development of acute and chronic inflammatory responses, as it can sense a wide range of aggregated molecules. There are other inflammasomes—such as absent in melanoma 2 (AIM2), NLRP1 and NLRP2—that might have a pathological role in the brain.

Activated microglia are characterized by the retraction of their processes, which is a phenotypic change that may correlate with an impaired ability to remodel synapses. This effect, along with the suppressive effects of cytokines and NO, may contribute to impaired synaptic plasticity in neurodegenerative disease. Furthermore, neuroinflammation restricts the supply of neurotrophic factors to glial cells and likely affects physiological processes that are important for intraneuronal protein handling. Microglial cell-driven neuroinflammation may not only affect neurons but may also cause detrimental feedback effects on microglia in the diseased tissue. For example, sustained exposure to pro-inflammatory mediators restricts microglial phagocytosis of misfolded and aggregated proteins.

Without being bound to any particular mechanism, pathogens, including β-amyloid plaques, are thought to trigger the formation of TLR-2-TLR-6 in microglial cells. TLR-2-TLR-6 augments NF-kB signaling which leads to the assembly of inflammasomes. Inflammasomes then produce cytokines and pro-inflammatory factors including one or more of IL-1β, TNF, IL12p40, IL-12, and IL-23. In some embodiments, the combination of levocetirizine and montelukast disrupt this inflammatory cascade by interfering with the activation of NF-kB. In some embodiments, the combination of levocetirizine and montelukast disrupt this inflammatory cascade by interfering with the release of one or more of IL-1β, TNF, IL12p40, IL-12, and IL-23. In some embodiments, the combination of levocetirizine and montelukast prevent inflammation associated with one or more of Alzheimer's disease, dementia, dementia with Lewy bodies, Parkinson's, Amyotrophic lateral sclerosis, frontotemporal dementia, and Huntington's disease. In some embodiments, the combination of levocetirizine and montelukast decrease cytokine levels that contribute to the pathology of one or more of Alzheimer's disease, dementia, dementia with Lewy bodies, Parkinson's, Amyotrophic lateral sclerosis, frontotemporal dementia, and Huntington's disease. In some embodiments, the combination of levocetirizine and montelukast block inflammation caused by microglial cell activation.

Levocetirizine offers a short time to peak plasma level, 0.9 hr., a short time to steady state level, 40 hours, a low volume of distribution, 0.4 L/kg, and an enhanced receptor affinity of 5× over first generation mepyramine in an acidic pH (many acute inflammatory disease states are associated with acidosis, a low physiologic pH). Levocetirizine has a 24 hour receptor occupancy of ~75%, the highest of the commercially available antihistamines. Receptor occupancy of the second generation antihistamines appears to correlate with the pharmacodynamic activity in skin wheal and flare studies and with efficacy in allergen challenge chamber studies. Levocetirizine has been objectively established a potent antihistamines through histamine induced wheal and flare data. For example, levocetirizine at 5 mg per day is more effective than fexofenadine at its commonly prescribed dose of 180 mg per day in the United States. In Europe the adult dose is 120 mg per day. Levocetirizine has a lower volume of distribution, greater histamine receptor affinity in an inflamed state (low pH), and greater receptor occupancy at 24 hours at physiologic doses than fexofenadine. The corresponding values are shown in Table 4.

TABLE 4

COMPARISON BETWEEN FEXOFENADINE AND LEVOCETIRIZINE

| | Fexofenadine | Levocetirizine |
|---|---|---|
| Vd-L/kg | 5.6 L/kg | 0.4 L/kg |
| Receptor affinity in an acidic ph | increased 2x | increased 5x |

TABLE 4-continued

COMPARISON BETWEEN FEXOFENADINE AND LEVOCETIRIZINE

|  | Fexofenadine | Levocetirizine |
|---|---|---|
| Histamine receptor occupancy at 24 hours | ~25% | ~75% |
| Steady-state level | 3 days | 40 hours |

Leukotriene $D_4$ is the most potent of the cysteinyl leukotrienes in contracting airway smooth muscle. Leukotriene receptors, such as $CysLT_1$, are found throughout the cells of the respiratory tree (including airway smooth muscle cells and airway macrophages) as well as on other pro-inflammatory cells in the body, particularly eosinophils and certain myeloid stem cells. Leukotrienes also function to promote the recruitment of eosinophils, dendritic cells and T cells. Eosinophil infiltration is considered by some authorities as a hallmark of inflammation.

Montelukast is FDA approved in the US for the treatment of perennial allergic rhinitis, asthma, seasonal allergic rhinitis, and exercised induced bronchospasm. Montelukast has been shown to be ineffective in improving asthma control or cold symptom scores caused by experimental rhinovirus infection. Unlike levocetirizine, no decrease in viral shedding was observed in rhinovirus-infected individuals treated with montelukast and there was no significant difference in reported cold symptom scores compared to placebo-treated individuals. Analysis of secondary outcomes suggests that montelukast may protect against reductions in lung function and increases in sputum eosinophils caused by common cold infections. During the recovery phase the percentage of sputum eosinophils was elevated in the placebo group, while the montelukast group remained at baseline levels. Further, peak expiratory flow was not decreased in the montelukast-treated patients. Montelukast treatment has no effect on the respiratory symptoms of patients with acute respiratory syncitial virus bronchiolitis. However, some studies indicate that treatment with montelukast reduced the number of days with worsened asthma symptoms and unscheduled doctor's visits in children with mild allergic asthma and resulted in a modest reduction of symptoms in children with recurrent wheezing when given at the first sign of upper respiratory tract illness.

Montelukast reaches a steady state level, like the second generation antihistamine, levocetirizine, in less than two days. Unlike other currently available leukotriene modulators, zileuton and zafirlukast, routine monitoring of liver function tests is not required. There are no drug interactions with warfarin, theophylline, digoxin, terfenadine, oral contraceptives, or prednisone.

The two molecules are safe, i.e., FDA approved in the United States for allergic disorders down to age six months. They can be given instead of or in conjunction with existing therapeutic protocols for the treatment of, including but not limited to, the Ebola virus, the Dengue virus, the West Nile virus, the Yellow fever virus, and the TBE virus. Levocetirizine and montelukast can also be given instead of or in conjunction with existing therapeutic protocols for inflammation related to, including but not limited to, the Ebola virus, the Dengue virus, the West Nile virus, the Yellow fever virus, and the TBE virus.

Both medications are pregnancy category B (Table 5).

TABLE 5

PREGNANCY CATEGORY DEFINITIONS

| Category | Definition | Explanation |
|---|---|---|
| A | Generally acceptable | Controlled studies in pregnant women show no evidence of fetal risk. |
| B | May be acceptable | Either animal studies show no risk but human studies not available or animal showed minor risks and human studies were done and showed no risk. |
| C | Use with caution if benefits outweigh risks | Animal studies show risk and human studies not available or neither animal nor human studies were done. |
| D | Use in life-threatening emergencies when no safer drug is available | Positive evidence of human fetal risk. |
| X | Do not use in pregnancy | Risks involved outweigh potential benefits. Safer alternatives exist. |

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes. Antipyretics as a class have been shown in a meta-analysis to increase the mortality rate in influenza animal models.

Steroids, which are widely used to treat inflammation, have significant short and long-term side-effects (Table 6). With regard to treating inflammation associated with rhinosinusitis, nasal steroids have their limitations, particularly in the elderly and those patients on aspirin, clopidogrel or warfarin prescribed to reduce the risk of stroke and heart attack. Even in patients who do not take these traditional "blood thinners," the risk of spontaneous epistaxis from nasal steroid sprays is between 4-22%. The risk of epistaxis is medication dependent. Epistaxis is a significant consideration in many patients 55 or older.

TABLE 6

STEROID SIDE EFFECTS

| Short term | Long term |
|---|---|
| Increased propensity for opportunistic infection | Glaucoma |
|  | Cataracts |
| Increased blood pressure | High-blood pressure |
| Mood changes | Heart disease |
| Increased blood sugar | Diabetes mellitus |

TABLE 6-continued

STEROID SIDE EFFECTS

| Short term | Long term |
| --- | --- |
| Increased intraocular pressure | Obesity |
| Water retention | Acid reflux/GERD |
| Weight gain | Osteoporosis |
| Increased risk for congestive heart failure | Myopathy |
| Flushing | Increased propensity for opportunistic infection |
| Increased appetite | |
| Insomnia | Cushing syndrome |

The typical daily dosage for levocetirizine is 5 mg for adults, and levocetirizine exhibits the following advantageous properties: i) Short time to reach peak plasma levels—0.9 hr; ii) Short time to steady state level—40 hrs; iii) Low volume of distribution (goes directly to the target receptor); iv) High receptor occupancy at 24 hours ~75%; v) Increased receptor affinity in inflamed tissue (acidic pH; up to 5× that of first generation molecules); vi) Pregnancy category B; vii) FDA approved down to six months for other disease states, i.e., perennial allergic rhinitis and chronic idiopathic urticaria; viii) Anti-inflammatory properties; and ix) immunologically modulated anti-viral properties. Studies in humans have shown that doses of levocetirizine up to 30 mg/day can be safely administered.

Montelukast, a leukotriene receptor antagonist, acts concurrently to protect the respiratory tree as well as block mediators in the inflammatory cascade. The typical daily dosage of montelukast is 10 mg for adults, and montelukast exhibits the following advantageous properties: i) montelukast is a selective receptor antagonist, inhibiting the physiologic action of $LTD_4$ at the $CysLT_1$ receptor; ii) montelukast binds with high affinity and selectivity to the $CysLT_1$ receptor without producing any agonist activity; iii) montelukast is rapidly absorbed; iv) montelukast reaches a peak plasma concentration in 3-4 hours; v) the oral bioavailability and $C_{max}$ of montelukast are not affected by a standard meal; vi) montelukast has a linear pharmacokinetics to 50 mg; vii) doses as low as 5 mg in adults cause substantial blockage of $LTD_4$-induced bronchoconstriction; viii) in a placebo controlled crossover study, montelukast inhibited early-phase bronchoconstriction due to antigen challenge by 75%; ix) montelukast is FDA approved down to six months of age; and x) montelukast has no drug interactions with warfarin, theophylline, digoxin, terfenadine, oral contraceptives, or prednisone. Montelukast has been administered at doses up to 200 mg/day to adult patients for 22 weeks and in short-term studies, and up to 900 mg/day to patients for approximately one week without clinically relevant side effects.

Accordingly, both levocetirizine and montelukast are pregnancy category B in the United States and are FDA approved in the United States down to six months of age for other disease processes. Moreover, both drugs have only once daily dosing, and no routine monitoring of blood work is necessary for most clinical situations. Further, both drugs exhibit minimal clinically relevant interactions with other medications. As described herein, both levocetirizine and montelukast [administered orally] reach steady state levels within two days to rapidly produce a synergistic and complementary anti-inflammatory effect.

Here, we describe the unexpected synergistic effects of combining levocetirizine and montelukast. Not wishing to be bound by a particular theory, a detailed examination of the pharmacokinetics of levocetirizine at the cell level illuminates the unique inflammatory properties that extend beyond the IgE mediated release of histamine including those pathways disclosed elsewhere herein. Levocetirizine exhibits a low volume of distribution (0.4 L/kg), prolonged dissolution time from the H1 receptor in an acidic pH, enhanced receptor affinity as a pure isomer of cetirizine, and the highest receptor occupancy at 24 hours of any currently available antihistamine. Such parameters impart an inflammatory effect by down regulating various ligands and cytokines including but not limited to IL-4, IL-6, IL-8 as well as cellular adhesion molecules and ligands as discussed elsewhere herein. The later are a homogeneous group of inducible immunoglobulins, integrins and selectins involved in cell-to-cell adhesion, cellular recruitment, homing and healing. In addition and as described above, levocetirizine has been shown in vivo to decrease ICAM-1, IL-6, IL-8, TLR3 expression and NF-kappa B activation resulting in decreased viral titers (e.g., human rhinovirus titers by log-2). A one log reduction in viral shedding results in a significant clinical benefit in virally-infected patients. Many virus serotypes share the same cellular receptor identifying ICAM-1 as the portal of entry into the cell. Levocetirizine inhibits virus-induced ICAM-1 and cytokine expression and viral replication. Experimentally, montelukast has been shown to decrease levels of soluble serum ICAM-1 (sICAM-1).

An unmet clinical need exists for the treatment of Ebola virus, West Nile infection, Dengue fever, Yellow Fever, and/or TBE. Not wishing to be bound by a particular theory, the steroid model suggests that levocetirizine acts in a non-IgE-mediated capacity at the level of NF-kB (See FIG. 2) and montelukast acts at the CysLT1 receptor to inhibit inflammation. In some embodiments, inflammation is inhibited by blocking the physiologic actions of LTD4. Both molecules are known to reduce the quantity of eosinophils and neutrophils/migration to site of inflammation. Montelukast, in addition, also decreases the recruitment of dendritic cells and T cells and other inflammation-related cells, an important concept to the overall approach to treating Ebola virus, West Nile infection, Dengue fever, Yellow Fever, TBE, Alzheimer's disease, dementia, dementia with Lewy bodies, Parkinson's, Amyotrophic lateral sclerosis, frontotemporal dementia, and Huntington's disease.

The actions of levocetirizine plus montelukast surpass the individual physiologic mechanisms of each, well beyond the treatment of allergic rhinitis and asthma. At least in part, it is the immunologically modulated anti-viral and anti-inflammatory properties of levocetirizine vis-a-vis NF-kB, IL-6, ICAM-1, RANTES; the inhibition of the actions of LTD4 by montelukast, underscored by ability of both levocetirizine and montelukast to inhibit the eosinophil and neutrophil quantity/migration, which impart synergy in the treatment of viruses selected from the group consisting of Ebola virus, West Nile infection, Dengue fever, Yellow Fever, TBE, Alzheimer's disease, dementia, dementia with Lewy bodies, Parkinson's, Amyotrophic lateral sclerosis, frontotemporal dementia, and Huntington's disease. This synergy is reflected by significantly improved clinical outcomes in a myriad of acute and chronic inflammatory disease states including but not limited to Ebola virus, West Nile infection, Dengue fever, Yellow Fever, and TBE.

Mechanism of Actions—Synergy within the Inflammatory Pathway Antihistamine, Leukotriene Receptor Antagonist, NF-kB, IL-6, I-CAM-1, IL-4, IL-8, Eosinophils, RANTES, TLR3, AP-1.

Nuclear factor-k B as a family of transcription factors plays a critical role in mediating responses to a remarkable diversity of external stimuli (see elsewhere herein). In some embodiments, administration of a therapeutically effective amount of the combination of levocetirizine and montelukast can be used in a method of treating each of the conditions disclosed above, including one or more of Ebola virus, West Nile infection, Dengue fever, Yellow Fever, and TBE. In some embodiments, administration of a therapeutically effective amount of the combination of levocetirizine and montelukast can be used in a method of treating each of the conditions disclosed above and in, for instance, Tables 1-3, including one or more of Influenza (A and B) virus, vesicular stomatitis virus, human immunodeficiency virus, Sendai virus, lactate dehydrogenase-elevating virus, mouse mammary tumor virus, murine leukemia virus, reoviridae, respiratory syncytial virus, coxsackievirus (B3 and B4), poliovirus, Punta toro virus, Measles virus, lymphocytic choriomeningitis virus, hepatitis C virus, Newcastle disease virus, nipah virus, rabies virus, Lassa virus, Lymphocytic choriomeningitis virus, Rift Valley fever virus, Japanese encephalitis virus, Rotavirus, Encephalomyocarditis virus, Theiler's virus, Mengovirus, Murine hepatitis virus, Murine norovirus 1, and Parainfluenza virus. This family of transcriptional factors (NF-kB) is a pivotal element across the spectrum of inflammation, immunity, cell proliferation, differentiation, and survival. NF-kB is expressed in almost all cell types and tissues. Specific binding sites are present in the promoters/enhancers of a large number of genes. Table 7 lists the remarkable array of NF-kB target genes.

TABLE 7

NF-kB Target Genes

Cytokines/Chemokines and their Modulators
Immunoreceptors
Proteins Involved in Antigen Presentation
Cell Adhesion Molecules
Acute Phase Proteins
Stress Response Genes
Cell Surface Receptors
Regulators of Apoptosis
Growth Factors, Ligands and their Modulators
Early Response Genes
Transcription Factors and Regulators
Viruses
Enzymes
Courtesy Boston University Biology One example of the influential nature the NF-kB family of transcription factors is RANTES (regulated on activation, normal T cell expressed and secreted) In the 'late' or adaptive phase of the immune response, RANTES is a chemokine generally expressed three to five days after T-cell activation. RANTES expression, mediated exclusively through NF-kB, attracts eosinophils, monocytes, mast cells and lymphocytes, activates basophils and induces histamine release from these cells.

Select H1 receptor antagonists (e.g., levocetirizine) have the remarkable ability to inhibit nuclear factor kappa-B (NF-kB) and activator protein-1 (AP-1) activity though H1 receptor—dependent and independent mechanisms. The induction of AP-1 and NF-kB activity by mizolastine and desloratadine required overexpression of the H1 receptor in a dose-dependent manner to decrease the tumor necrosis factor-α production of the chemokine, RANTES. Diphenhydramine, the prototype first generation antihistamine, H2 and H3 receptor antagonists were ineffective.

Mizolastine has not been approved in the United States. Although the bioavailability of mizolastine is high and the drug is mainly metabolized via glucuronidation, systemic dosing of ketoconazole and erythromycin moderately increases the plasma concentration of mizolastine.

As such, concomitant use is therefore contraindicated. The concomitant use of other potent inhibitors or substrates of liver oxidation (cytochrome P450/3A4) with mizolastine must be carried out with caution. Approximately 50% of commonly prescribed medications are metabolized via the cytochrome P450 3A4 or 2D6 pathways in the liver.

Desloratadine, the long-acting tricyclic metabolite of loratadine, is extensively metabolized through the CYP P450 3A4 and 2D6 pathways. The half-life of 27 hours increases to >50 hours in slow metabolizers (7% of the Caucasian and 20% of the African-American population). Moreover, in a double-blind, placebo controlled crossover study, levocetirizine was 8× more effective in inhibiting wheal and flare responses in the skin. The pharmacokinetics of both mizolastine and desloratadine do not support their use in acute and critical care medicine.

Levocetirizine has been shown to inhibit human rhinovirus (HRV)-induced ICAM-1, cytokine expression, and viral replication in airway epithelial cells from both the nose and lung. Overexpression of the H1 receptor in the laboratory resulted in the inhibition of the HRV-induced upregulation of ICAM-1, Il-6, TLR3 expression and NF-kB activation. Levocetirizine reduced the levels of HRV-induced increases in ICAM-1 regardless of whether the levocetirizine was added before, after, or at the time of the HRV infection. The results were in agreement with previous research on the inhibitory effects of levocetirizine ICAM-1 up-regulation.

In some embodiments, the methods described herein involve identifying a patient in need of treatment. Once identified, the patient the combination of levocetirizine and montelukast is administered to the patient for a period of time. In some embodiments, the administration of the combination can be terminated at a time when the combination is no longer needed.

In some embodiments, the period of administration comprises a period starting when the patient first displays symptoms until a time when the viral infection or disease state is controlled or cured (e.g., the acute symptoms have subsided, viral titers have decreased to a baseline, risk factors for disease or viral progression have decreased, etc.). In some embodiments, the period of time comprises a period spanning from when the patient or doctor suspects the patient has been exposed to a virus to a time when the patient is no longer at risk of developing acute infection from that virus. In some embodiments, the combination of levocetirizine and montelukast is given to alleviate symptoms of a chronic disease and the combination is given for the duration of the disease state (e.g., for the lifespan of the patient). In some embodiments, the combination of levocetirizine and montelukast is administered preventatively for a period during high exposure risk or during a period when the disease is likely to display symptoms.

In some embodiments, patients in need of treatment include those who are at risk for being exposed to viral infection (e.g., by traveling to areas where infectious outbreaks are occurring or have occurred in the past). In some embodiments, patients in need of treatment can include those who are at a high likelihood of developing diseases states because of genetic factors or due to lifestyle variables (e.g., former drug users, people who are prone to concussion or have suffered multiple concussions, those who have family members with neurologic diseases, etc.). In some embodiments, for those at risk patient groups, the combination of levocetirizine and montelukast can be administered after age 30, 40, 50, 60, 70, 80, 90, or above, throughout the rest of the patient's life.

In some embodiments, the patients comprise any type of mammal (e.g., humans, cows, sheep, horses, cats, dogs, goats, rodents, etc.).

In some embodiments, the levocetirizine montelukast combination is administered in a sequential manner. In some embodiments, levocetirizine is administered first. In some embodiments, montelukast is administered first. In some embodiments, the combination is administered in a substantially simultaneous manner.

In some embodiments, levels of levocetirizine utilized in the laboratory model can be safely achieved in a clinical setting; however, are above the standard adult dose of 5 mg daily used for the treatment of allergy and asthma. In some embodiments, the addition of montelukast, also above the standard 10 mg adult dose for allergy and asthma results in a remarkable synergistic effect which has been shown in our clinical setting to safely decrease the symptoms and duration of the viral infection.

In some embodiments, the combination is administered to the patient by one or more of the routes consisting of enteral, intravenous (including, but not limited to a long-acting injectable, e.g., an extended release preparation), intraperitoneal, inhalation, intramuscular (including, but not limited to a long-acting injectable, subcutaneous and oral). In some embodiments, the levocetirizine and montelukast are administered by the same route. In some embodiments, the levocetirizine and montelukast are administered by different routes. In some embodiments, the combination is dosed to the patient using an effective amount of a combination of levocetirizine and montelukast.

In some embodiments, dosing and delivery of the combination of levocetirizine and montelukast can be performed for periods between five days—twelve months to achieve continuous tissue levels of the drug combination. In some embodiments, dosing and delivery of levocetirizine and montelukast can be performed for periods of at least about 1 day, 5 days, 10 days, 20 days, 30 days, 50 days, 100 days, 200 days, 300 days, ranges and values between the aforementioned values and otherwise. In some embodiments, the rationale is to achieve sustained tissue levels to modulate NF-kB at multiple targets within the immune system (Constant overexpression of the H1 Receptor).

In some embodiments, levocetirizine and montelukast are provided in long-acting delivery formats to treat the viruses. In some embodiments, the levocetirizine and montelukast are provided in once-daily or multiple-daily doses. In some embodiments, traditional oral delivery systems: film strips, bilayer tablets, capsules, tablets, nebulized therapy, etc. could be utilized if administered on at least a twice daily regimen, early in the course of the disease, i.e., the first seventy-two hours. Otherwise, with the onset of nausea and diarrhea, or manifestation of any of the systemic indicators: (a) shortness of breath, (b) hypotension, (c) bleeding, (d) coma, an IV (intravenous), IM (intramuscular) or LAI (long-acting injectable) can be successful in changing the outcome (e.g., EBOLA).

Depending upon the patient's age, weight, BMI (body mass index) and severity of the disease on presentation, the dosing (oral, IV, IM) or dose (LAI) can be titrated to effect over the following range:

Levocetirizine: 1.25-30 mg/24 hours

Montelukast: 4 mg-50 mg/24 hours for a duration of at least five days

Computer modelling should allow for precise dosing and delivery which will vary depending upon the nature and extent of the clinical presentation.

Given the half-lives of the molecules and other pharmacokinetic considerations, once oral daily dosing, particularly in an acutely ill patients, may not be effective. As such, in some embodiments, in a difficult-to-treat or harsh environment, a long-acting injectable may be employed. In some embodiments, a formulation (e.g., a long-acting injectable) comprising 50-100 mg of levocetirizine and 100-200 mg of montelukast within a pharmaceutically acceptable medium or as a pharmaceutically acceptable medium (e.g., reconstituted lyophilized powder) is dosed to maintain a steady state level for seven days. In some embodiments, the injectable can be configured to deliver the oral equivalent of between 5 mg and 20 mg of levocetirizine and between 10 mg and 40 mg of montelukast to the patient per day (depending on the nature and extent of the disease process; taking into consideration patient weight, age, etc.). In some embodiments, oral dosing can also be used where appropriate dosing between 5 mg and 20 mg of levocetirizine and between 10 mg and 40 mg of montelukast/day, respectively. Divided oral daily dosing may be employed. In some embodiments, the formulation comprises about 50 mg, about 100 mg, about 150 mg, about 200 mg, about 300 mg, about 400 mg, about 500 mg, or more of levocetirizine. In some embodiments, the formulation comprises about 50 mg, about 100 mg, about 150 mg, about 200 mg, about 300 mg, about 400 mg, about 500 mg, or more of montelukast.

In some embodiments, long-acting comprises injectables that peak in a short period of time (e.g., within about 1-3 hours, or less than about 1 hour, about 2 hours, about 3 hours, about 4 hours, about 5 hours, ranges between those values or otherwise). In some embodiments, long-acting injectables are those that maintain a nearly constant plasma or CNS level for a sustained period of time (e.g., about 3 days, about 4 days, about 5 days, about 6 days, about 7 days, about 14 days, about 21 days, about 28 days or more, ranges between those values or otherwise). In some embodiments, a nearly constant blood concentration is one that is about 25 ng/mL (combined plateau of both drugs), about 50 ng/mL, about 150 ng/mL, about 250 ng/mL, about 350 ng/mL, about 450 ng/mL, about 550 ng/mL, about 650 ng/mL, or more (plus or minus about 25-50 ng/mL).

In some embodiments, oral BID dosing can be used to saturate levocetirizine and montelukast receptors in an estimated ratio of 3 mg/6 mg (respectively) one in the AM and two HS (e.g., for Dengue, Yellow Fever, and TBE. Separately, 6 mg/12 mg at night for long-term treatment of HIV. In some embodiments, for the innate CNS disorders (e.g., Alzheimer's, Parkinson's disease and ALS) therapy would be long-term, months to years, qd to bid with an optimal daily dosing range of 6-8 mg/12-18 mg: levo/monte; titrated to effect from monthly to quarterly patient visits, neuropsychiatric assessments at six month intervals and QOL questionnaires at each patient visit. In some embodiments, both molecules cross the blood-brain barrier at 0.1 mg/kg. In some embodiments, lower (or higher) dosing could be used.

In some embodiments, the treatments described above further comprise the administration of a steroid.

The technology has evolved to repurpose levocetirizine+ montelukast in a long-acting injectable. This concept is particularly useful where the patient (a) is unable to swallow, (b) where there are limited resources for overall care and management, (c) for prophylaxis in a pandemic, and (d) for use as a bioterrorist counteragent.

Predictive modelling software can be utilized to take existing information on the API (active pharmaceutical ingredient), excipients, the desired release profile, and end environment (body v CNS) and calculate a formulation which can then be used to manufacture microparticles that encapsulate the API and release it at the desired rate. Using computer metrics, the laboratory to manufacturing formulation variances can be minimized during the design phase.

Delivery vehicles include but are not limited to injectable microparticles, nanoparticles, matrix implants, and device coatings. Release profiles can be designed as constant rate (where doses are released at desired profiles for a period of days, weeks, or months), delayed release, or sequential release. In some embodiments, a wide variety of controlled release systems can be formulated. In some embodiments, the delivery vehicle is an selected from the group consisting of injectable microparticle, nanoparticles, pellets, rods discs, tablets, thin film coatings, matrix implants, device coatings, and combinations thereof. In some embodiments, the delivery vehicle formulated from one or more of Poly(lactic-co-glycolic acid) (PLGA), Polyanhydrides (PSA, PSA:FAD), Polylactides (PLA), Poly-ortho-esters (POE), or HPMC hydrogels. The release profile can be tailored between Constant Rate (days, weeks, months), Delayed Release, and Sequential Release.

Proactive inhibition of recognition receptors, for example, the Rig-I-like receptor (RLR) in the treatment of EBOLA virus (and/or one or more of West Nile virus, Dengue virus, tick borne-encephalitis, HIV, and Yellow Fever virus, or their respective receptors: West Nile virus—at least RIG-I, TLR3; Dengue virus—at least RIG-I, MDA5, TLR7; TBE virus—at least TLR3; HIV—at least TLR7, TLR8; Yellow Fever—at least TLR 7) is an important tenet. Similarly efficacious is the proactive inhibition of pathogen recognition receptors (PRRs), for example, the toll-like receptors in the treatment of parasites (e.g., Malaria and its respective receptors—at least TLR7, TLR9). This concept is supported by the observation that preactivation (or treatment prior to exposure in a clinical setting) of RIG-I reduces EBOV titers in cell culture up to ~1000-fold. Clinically, the magnitude of the viremia has been correlated with host survival. Patients with fatal outcomes had higher viral loads, i.e., median tissue culture infective doses ($TCID_{50}$/ml) of ~$10^5$-$10^6$ contrasted to $10^3$-$10^4$ in survivors. The combination of levocetirizine and montelukast can be designed in multiple formats as a bioterrorist counteragent.

TCID50/ml is the measure of infectious virus titer. This endpoint dilution assay quantifies the amount of virus required to kill 50% of infected hosts or to produce a cytopathic effect in 50% of inoculated tissue culture cells.

Levocetirizine and montelukast also can be used for in the treatment of HIV: (For instance, an HIV patient with significantly improved CD4 cell counts (objective measurable data) and additionally the absence of respiratory tract infections at 2+ years (i.e., the combined therapy is also prophylactic against the common cold) on long-term levocetirizine+montelukast therapy with no interval change in HIV retroviral medications).

In addition to the viruses, parasites and diseases above, the combination of levocetirizine and montelukast can be used it the treatment of other viruses and diseases as well. Combination therapy could potentially be applied to any NF-kB dysregulated pathway to improve quality of life or to treat viral infection and disease. In some embodiments, a medicament comprising levocetirizine or the combination of levocetirizine and montelukast is used in a method of treating a condition that is, at least in part, mediated by the NF-KB pathway.

For example, some embodiments pertain to the treatment one or more of Alzheimer's disease, dementia, dementia with Lewy bodies, Parkinson's, Amyotrophic lateral sclerosis, frontotemporal dementia, and Huntington's disease by administering a medicament comprising levocetirizine, or the combination of levocetirizine and montelukast to a patient.

Turning to neuroscience, it has been shown that animal subjected to traumatic brain injury can exhibit elevated levels of NK-kB for up to one year. Activation of the NOD, NLRP3 inflammasome by aberrant host proteins (the latter of which would also exist in an EBOV infection) is a common step in the development of a diverse array of neurodegenerative disorders. Understanding that M1-like activated microglial cells are responsible for chronic brain inflammation, structural damage to neurons, and neuronal dysfunction, with a resultant poor neurological outcome, LAI therapy in a TBI animal model would decrease microglial cell activation through NF-kB.

Separately in a mouse model of amyotrophic lateral sclerosis (ALS), classic NF-kB activation was required to induce motor-neuron death. The extent of microglial cell activation positively correlated with the severity of the clinical symptoms.

EXAMPLES

Example 1

Ebola Virus

Based on the inventor's clinical experience using levocetirizine and montelukast, the following results are projected using controlled studies.

A cohort of 40 patients between the ages of 15-30 years of age (with no other co-morbid viral or disease processes) infected with Ebola Virus is identified. Each patient is identified as having an Ebola symptom (e.g., one or more of headache, fever, fatigue, myalgia, gastrointestinal distress, and hemorrhage) ideally within the first 48 hours of symptom onset. The experimental group patients (n=20; "EXPT") receives levocetirizine and montelukast. The control group patients (n=20; "CONT") receive conventional treatments for EBOLA infection.

Age, sex, race, height, weight, BMI (Body Mass Index/ kg/m$^2$), vital signs, major medical problems, medications, allergies to medications, cigarette and alcohol use, social history, and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero— first dose of medication(s)).

Depending upon the treatment location (e.g., Africa) the following studies and special chemistries may not be available. If available, the following testing is performed.

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3, ICAM-1, sICAM-1, RIG-I

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNɣ; IL-10; Interleukin 12p70 (IL-12p70); IL12p40; Interleukin 1α (IL-1α); IL-1β; IL-1 receptor antagonist (IL-1RA); IL-2; IL-4; IL-5; IL-6; IL-8; IFN-ɣ-inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. The above markers are used to analyze patient response and further define the mechanism of the medication. In some embodiments, one or more of the above cytokines, chemokines, biomarkers of inflammation, and biomarkers for coagulopathy return to normal/non-infected levels at an accelerated rate versus CONT groups.

For levocetirizine, peak concentrations are typically 270 ng/ml and 308 ng/ml following a single and repeated 5 mg once daily oral dose, respectively.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

Given the half-lives of the molecules and other pharmacokinetic considerations, once daily oral dosing, particularly in an acutely ill patient with nausea and vomiting, may not be effective. As such, particularly in a difficult-to-treat or harsh environment, a long-acting injectable may be employed. For instance, a long acting injectable comprising 50-100 mg of levocetirizine and 100-200 mg of montelukast within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day (depending on the nature and extent of the disease process; taking into consideration patient weight, age, etc.). Oral dosing can also be used where appropriate to achieve similar blood levels (e.g., daily, bid, tid, or more).

With a mortality rate of up to 90% it would be considered unethical by international standards (World Health Organization) to conduct a placebo arm. As such, 10 EXPT patients would receive a long-acting injectable preparation (computer modeled on a mg/kg basis) to deliver a sustained plasma level of both levocetirizine and montelukast in the range of 350 ng/ml for 7 days (the EXPT1 group). The second group of 10 patients would receive a higher dose to sustain plasma levels in the range of 500 ng/ml for a period of 7 days (The EXPT2 group), while the CONT group receives conventional EBOLA abatement treatments. The EXPT1 and EXPT2 groups also receive conventional EBOLA supportive measures in addition to the levocetirizine and montelukast combination.

Outcomes

The primary endpoint of the study is the percentage reduction in mortality when compared to age and symptom matched controls at time zero as determined from the WHO database. The long-acting injectable is found to decrease in the mortality by up to 25% base on published mortality rates of 57-90%. A dose-response curve trending favorably to the higher high mean serum concentration range of 500 ng/ml. Levels of IL-6 (attenuated by levocetirizine) directly correlate with mortality.

Secondary endpoints are: (a) abatement of the hemorrhage and (b) mean time to clinical resolution.

Hemorrhage is considered an independent variable with no statistically significant difference between hemorrhage and death; however, hemorrhage does statistically correlate with the concentration of soluble ICAM-1 (sICAM-1). Experimentally, montelukast has been shown to decrease the levels of sICAM-1.

In summary, treatment of EBOLA with a long-acting injectable containing levocetirizine and montelukast will significantly decrease the morbidity and mortality associated with the disease.

Patients receiving the levocetirizine and montelukast exhibit less severe symptoms. Patients report, on a pain intensity scale (0-10), headaches that are 30% and 60% less intense and fatigue that is 40% and 70% less intense in the EXPT1 and EXPT2 groups, respectively, when compared to the CONT group. Also, 30% and 50% fewer patients display gastrointestinal distress in the EXPT1 and EXPT2 groups, respectively. Fever levels in EXPT1 and EXPT 2 groups are an average of 2 and 3° F. lower in the EXPT1 group and the EXPT2 group, respectively, than the CONT group after 2 days of dosing. In patients making a full recovery, the patients in the EXPT1 and EXPT2 group have normal temperatures on average 3 and 4 days faster than those in the CONT group, respectively.

By day 3 of treatment viral titers in EXPT1 and EXPT2 patients are, on average, 25% and 35% lower, respectively, than in the CONT group. In patients making a full recovery, the patients in the EXPT1 and EXPT2 groups are virus free (by measure of viral titers) on average 3 and 4 days faster than those in the CONT group.

The death rate for the EXPT1 and EXPT2 groups at day 14 is 25% and 30% lower, respectively, than the CONT group. Of the survivors, those in the EXPT1 and EXPT2 groups have 30% and 40% lower incidences of prolonged secondary issues resulting from the acute infection, respectively. Incidences of hemorrhage decrease by 15% and 25% in the EXPT1 and EXPT2 groups, respectively, compared to the CONT group. Severity of hemorrhage decreases by 25% and 45% in the EXPT1 and EXPT2 groups, respectively, compared to the CONT group.

Example 2

EBOLA Virus/Levocetirizine and Montelukast as Adjunct Therapy to Existing Treatment/Novel Antiviral Based on the inventor's clinical experience using levocetirizine and montelukast, the following results are projected using controlled studies.

A cohort of 40 patients between the ages of 15-30 years of age (with no other co-morbid viral or disease processes)

infected with Ebola Virus are identified. Each patient is identified as having onset of Ebola symptoms (e.g., one or more of by the onset of headache, fever, fatigue, myalgia, gastrointestinal distress, and hemorrhage) ideally within the first 48 hours of symptom onset.

Age, sex, race, height, weight, BMI (Body Mass Index/ kg/m2), vital signs, major medical problems, medications, allergies to medications, cigarette and alcohol use, social history, and previous surgery are logged at the initial visit and the patient's symptom profile tracked in a controlled environment.

If possible an applicable quality of life questionnaire is filled out by the patient and health care provider.

Onset, duration and intensity of symptoms are logged in addition to the time to resolution of symptoms (time zero— first dose of medication(s)).

Depending upon the treatment location (e.g., Africa) the following studies and special chemistries may not be available.

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3, ICAM-1, sICAM-1, RIG-I;

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Then existing EBOLA medication(s) including any novel antiviral is logged into the patient record. The above markers are used to analyze patient response and further define the mechanism of the medication. In some embodiments, one or more of the above cytokines, chemokines, biomarkers of inflammation, and biomarkers for coagulopathy return to normal/non-infected levels at an accelerated rate versus CONT groups.

Dosing

With a mortality rate of up to 90% it would be considered unethical by international standards (World Health Organization) to conduct a placebo arm.

As such standard or novel EBOLA therapy (experimental or approved antiviral) is administered at the recommended dose (e.g. brincidofovir)

In the first treatment arm, half the patients, i.e., 20, are given the standard therapy or antiviral (e.g. brincidofovir) without the LAI containing levocetirizine and montelukast. In second arm of the study the standard therapy or antiviral (e.g., brincidofovir) is given in conjunction with the LAI containing levocetirizine and montelukast. The duration of the medications are predicated upon the nature and extent of the disease process upon presentation or the development of complications during treatment, i.e., the LAI (sustaining serum levels of approximately 350 ng/ml) may be required at seven day intervals for two to three sequential doses depending upon the status of the patient.

Side effects of the medication(s) are recorded for each treatment arm.

Anticipated is a more robust time to resolution, decreased morbidity and overall mortality rate when contrasted with like patients from the WHO database. Additionally anticipated are fewer overall side effects (e.g., nausea, urticaria, unanticipated changes in serum chemistries or blood count, headache, etc.).

In summary, treatment of EBOLA with standard therapy or a novel antiviral (e.g., brincidofovir) in conjunction with a LAI containing the combination of levocetirizine and montelukast, would enhance the effectiveness of that therapy in addition to mitigating side effects from the standard therapy or novel antiviral.

Example 3

West Nile Virus

Based on the inventor's clinical experience using levocetirizine and montelukast, the following results are projected using controlled studies.

A cohort of 40 patients between the ages of 20-30 years of age (with no other co-morbid viral or disease processes) infected with West Nile virus is identified. Each patient is identified as having West Nile viral infection symptoms (e.g., one or more of the following: fever, headache, fatigue, muscle pain or aches (myalgia), malaise, nausea, anorexia, vomiting, and rash) ideally within the first 48 hours of symptom onset. The experimental group patients (n=20; "EXPT") receives levocetirizine and montelukast as well as conventional West Nile therapies. The control group patients (n=20; "CONT") receive conventional therapies for treating West Nile alone.

Age, sex, race, height, weight, BMI (Body Mass Index/ $kg/m^2$), vital signs, major medical problems, medications, allergies to medications, cigarette and alcohol use, social history and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero— first dose of medication(s)).

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR7, RIG-I,MDA5, ICAM-1, sICAM-1;

Samples for chemokines, cytokines, biomarkers of inflammation, and biomarkers of coagulopathy. These include but are not limited to: Granulocyte macrophage colony stimulating factor (GM-CSF); GROα; Interferon α2

(IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. For levocetirizine, peak concentrations are typically 270 ng/ml and 308 ng/ml following a single and repeated 5 mg once daily oral dose, respectively. In extreme cases this can be doubled, tripled, otherwise increased. In mild cases, this amount can be halved, quartered, or otherwise reduced.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

Given the half-lives of the molecules and other pharmacokinetic considerations, once oral daily dosing, particularly in an acutely ill patient with nausea and vomiting, may not be effective. As such, particularly in a difficult-to-treat or harsh environment, a long-acting injectable may be employed. For instance, a long acting injectable comprising 50-100 mg of levocetirizine and 100-200 mg of montelukast optionally within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day for seven days (depending on the nature and extent of the disease process; taking into consideration patient weight, age, etc., e.g., mean serum concentration range of 500 ng/ml Oral dosing can also be used where appropriate to achieve similar blood levels.

The primary endpoint of the study is the percentage reduction in mortality when compared to age and symptom matched controls at time zero as determined from the WHO database. The long-acting injectable or oral dosing is found to decrease in the encephalitis by up to 50% based on published mortality rates.

The secondary endpoint is the mean time to clinical resolution.

Patients receiving the levocetirizine and montelukast exhibit less severe symptoms. Patients report, on a pain intensity scale (0-10), headaches and muscle pain are 50% less intense and fatigue is 60% less intense in the EXPT group when compared to the CONT group. Also, 40% fewer patients display vomiting in the EXPT group. Fever levels in EXPT group is an average of 3° F. than the CONT group after 2 days of dosing. In patients making a full recovery, the patients in the EXPT group have normal temperatures on average 3 days faster than those in the CONT group.

By day 4 of treatment, viral titers in EXPT patients are, on average, 35% lower than in the CONT group. In patients making a full recovery, the patients in the EXPT group are virus free (by measure of the viral load) on average 3 days faster than those in the CONT group.

Those in the EXPT group have 20% lower incidences of prolonged secondary issues resulting from the acute infection. Incidences of hemorrhage decrease by 25% in the EXPT group compared to the CONT group.

Example 4

West Nile Virus Case Study I

Overview:

West Nile virus is a mosquito borne virus for which there is currently no effective treatment. The disease is characterized by the sudden onset of an acute, nonspecific flu-like illness lasting 3-6 days, with high fever and chills, malaise, headache, backache, arthralgia, myalgia, and retro-orbital pain without overt neurological signs. Other non-specific features include anorexia, nausea, vomiting, diarrhea, cough and sore throat. A maculopapular rash has been reported in approximately 50% of cases.

Neurological disease occurs in fewer than 1% of infected individuals, with a typical prodrome of 1-7 days. Acute flaccid paralysis caused by the infection of the anterior horn of the spinal cord (myelitis) suggests a clinical picture of poliomyelitis; paralysis is frequently asymmetric and may or may not be associated with meningoencephalitis. Once paralysis has been established, little long-term improvement has been described in the literature.

The overall case fatality rate for hospitalized patients ranges from 4-14%.

West Nile virus receptors: RIG-I, TLR3

Name: JN

DOB: Mar. 24, 1976 Age at presentation: 36

Date of Exam: October 5

HPI: 36 year old male with a history of West Nile meningitis preceded by onset of backache and fatigue on September 7. The following day he was seen at an Urgent Care in Newport Beach, Calif. and given oseltamivir (Tamiflu®) 75 mg po bid×five days for a presumed case of influenza. By September 11 symptoms had progressed to include insomnia and severe mid-lower back pain radiating down the left side of his leg. On Wednesday, September 12, he returned to Urgent Care and was given oxycodone for pain scaled 7-8/10 in addition to ibuprofen 800 mg twice a day.

By September 14 the patient had developed a low grade fever to 100° F. with chills, myalgia, back pain, and fatigue. Over that weekend he could barely get out of bed. On September 15 he went to a different Urgent Care and was sent to the Emergency Department at Hoag Hospital, Newport Beach, Calif. The physicians discharged him on ciprofloxacin 500 mg, orally twice a day and oxycodone with a working diagnosis of acute prostatitis. By 10:30 PM that night he had developed nausea, confusion, and a fever to 102° F. The evening of September 16 he returned to Hoag Hospital in an ambulance and admitted for treatment of West Nile meningitis.

Hospital Stay—September 16-September 21

Over the two weeks prior to our visit on October 5 he was gradually improving; however, continued to exhibit marked fatigue, left lower extremity weakness, and pain in the lower back and left leg scaled 4/10. Flexeril® (cyclobenzaprine) was taken at night as a muscle relaxant. Physical therapy was ongoing in a frequency of twice a week.

Medications: Flexeril® (cyclobenzaprine) 10 mg, prn, multivitamins
  Allergies to Medications: none
  Additional major medical problems: none
  Surgery: none
  Habits:
  Cigarettes—none
  Alcohol—occasional use
  Occupational history: Commercial real estate
Pertinent Physical Examination: October 5
  VS: normal
  Weight: 188.9#/85.8.5 kg, previously 205#/93 kg
  General: polite male exhibiting significant fatigue and weakness for his stated age, gait unsteady
  Otherwise oriented to time, place and person.
  Subtle muscle wasting—left leg
  Left leg and lower back pain
  Ears: tympanic membranes—gray
  Nose: left deviated nasal septum, no erythema
  Throat: 2+/4+ tonsils, no evidence of acute infection
  Neck: without adenopathy
  Lungs: clear
  Cor: S1, S2 distinct, no murmur
Chart Review—Hoag Hospital Admission September 16-September 21
  Salient information:

| | | | | |
|---|---|---|---|---|
| CPK 803 | 09/15 (Hoag ED) - elevated, normal <300 IU/L, cardiac arrhythmia | | | |
| CXR - normal | 09/17 | 09/17 | | |
| Lumbar puncture | | | | |
| CSF protein | 108 mg/dl | normal 12-60 | elevated | |
| CSF glucose | 55 mg/dl | normal 40-70 | elevated | |
| CSF WBC | 519/cumm | | elevated | 09/20 |
| WBC | 3.6 K/uL | normal 4-10 | low* | 10/05 |
| Laboratory Data | | | | |
| Pacific Diagnostic Laboratories | | | | |
| 89 S. Patterson Ave. | | | | |
| Santa Barbara, Ca. Ca. 93111 | | | | |
| CBC | | | | |
| WBC* | 3.6 K/uL | normal 4-10 | | |
| Hgb | 14.3 g/dl | normal: 13-17 | | |

*low; consistent with a viral infection
Note:
continued suppression of the white blood cell count following discharge 09/21

Hct 42.2% WBC From Sep. 20, 2012-October 5

| | | |
|---|---|---|
| Platelet count | 173 K/uL | normal: 150-450 |
| CPK | 121 IU/L | normal: <300 |
| CRP | <4.0 mg/L | normal <10.0 |
| Sed rate | 4 mm/hr | normal 0.0-15.0 |
| Total IgE | 28.3 kU/L | normal 0-60 |
| West Nile Ab, IgM - positive | | |
| West Nile Ab, IgG - positive | | |
| Assessment: West Nile meningitis with fatigue, left lower extremity weakness and pain. | | |

Treatment: levocetirizine—5 mg po hs and montelukast—10 mg orally at night×six months to stabilize the inflammatory process and enhance recovery. Telephone call (October 25): feeling much better and stronger with significantly less fatigue and muscle weakness. Back to work. No side effects from the medication.

Advised to continue levocetirizine and montelukast through the end of March the following year.
Summary
This is a remarkable case of confirmed West Nile meningitis treated post discharge from the hospital with levocetirizine and montelukast. Physicians at Hoag Memorial Hospital had informed him it would take a year to fully recover. He clinically recovered in three weeks with no side effects.

West Nile virus has a variable presentation. Dosing for hospitalized patients would range from:
Therapeutic Dosing for Acute Disease:
  levocetirizine 10-20 mg, divided dose bid, or in an injectable format to achieve sustained serum levels of at least 350 ng/ml plus
  montelukast 20-40 mg/day, divided dose bid, or in an injectable format to achieve sustained dosing of at least 350 ng/ml.
  Higher total daily dosing would be required to treat meningitis or meningoencephalitis
  Both medications, if so required, cross the blood brain barrier at a dose of 0.1 mg/kg.
Therapeutic Dosing During the Convalescent Phase of the Disease:
  The long-term convalescent dose used in the present case was levocetirizine—5 mg, orally, and montelukast 10 mg, orally once a day. More significant CNS pathology would require higher dosing.

Example 5

Dengue Fever

Based on the inventor's clinical experience using levocetirizine and montelukast, the following results are projected using controlled studies.

A cohort of 40 patients between the ages of 20-30 years of age (with no other co-morbid viral or disease processes) infected with Dengue Fever virus is identified. Each patient is identified as having Dengue symptoms (e.g., headache, muscle and joint pains, rash, nausea, vomiting, bleeding from the mucous membranes of the mouth and nose, leakage of plasma from the blood vessels, dengue shock syndrome, and hemorrhagic fever) ideally within the first 48 hours of symptom onset. The experimental group patients (n=20; "EXPT") receives levocetirizine and montelukast as well as conventional Dengue fever therapies. The control group patients (n=20; "CONT") receive conventional therapies for treating Dengue fever alone.

Age, sex, race, height, weight, BMI (Body Mass Index/ $kg/m^2$), vital signs, major medical problems, medications, allergies to medications, cigarette and alcohol use, social history, and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero—first dose of medication(s)).

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3, ICAM-1, sICAM-1, RIG-I

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ-inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. For levocetirizine, peak concentrations are typically 270 ng/ml and 308 ng/ml following a single and repeated 5 mg once daily oral dose, respectively. In extreme cases this can be doubled, tripled, otherwise increased. In mild cases, this amount can be halved or otherwise reduced.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

Given the half-lives of the molecules and other pharmacokinetic considerations, once daily oral dosing, particularly in an acutely ill patient with nausea and vomiting, may not be effective. As such, particularly in a difficult-to-treat or harsh environment, a long-acting injectable may be employed. For instance, a long acting injectable comprising 50-100 mg of levocetirizine and 100-200 mg of montelukast within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day for seven days (depending on the nature and extent of the disease process; taking into consideration patient weight, age, etc.). Oral dosing can also be used where appropriate to achieve similar blood levels.

The primary endpoint of the study is the percentage reduction in mortality when compared to age and symptom matched controls at time zero as determined from the WHO database. The long-acting injectable is found to decrease in the mortality by up to 50% base on published mortality rates with mean serum concentration ranges between 350-500 ng/ml. Levels of IL-6 (attenuated by levocetirizine) directly correlate with mortality.

Secondary endpoints are: (a) abatement of the symptoms and (b) mean time to clinical resolution.

Patients receiving the levocetirizine and montelukast exhibit less severe symptoms. Patients report, on a pain intensity scale (0-10), headaches and muscle pain are 50% less intense and fatigue is 70% less intense in the EXPT group when compared to the CONT group. Also, 30% fewer patients display vomiting in the EXPT group. Fever levels in EXPT group is an average of 3° F. than the CONT group after 2 days of dosing. In patients making a full recovery, the patients in the EXPT group have normal temperatures on average 5 days faster than those in the CONT group.

By day 4 of treatment, viral titers in EXPT patients are, on average, 35% lower than in the CONT group. In patients making a full recovery, the patients in the EXPT group are virus free (by measure of viral titers) on average 5 days faster than those in the CONT group.

Those in the EXPT group have 20% lower incidences of prolonged secondary issues resulting from the acute infection. Incidences of hemorrhage decrease by 25% in the EXPT group compared to the CONT group. Severity of hemorrhage decreases by 45% the EXPT group.

Example 6

Yellow Fever

Based on the inventor's clinical experience using levocetirizine and montelukast, the following results are projected using controlled studies.

A cohort of 30 patients between the ages of 20-35 years of age (with no other co-morbid viral or disease processes) infected with Yellow Fever virus is identified. Each patient is identified as having one or more symptoms (e.g., fever, headache, chills, back pain, fatigue, loss of appetite, muscle pain, nausea, vomiting, hematemesis, epistaxis nasal bleeding, gum bleeding, gastrointestinal bleeding, and icterus) ideally within the first 48 hours of symptom onset. The experimental group patients (n=15; "EXPT") receives levocetirizine and montelukast as well as conventional Yellow fever therapies. The control group patients (n=15; "CONT") receive conventional therapies for treating Yellow fever alone.

Age, sex, race, height, weight, BMI (Body Mass Index/ kg/m$^2$), vital signs, major medical problems, medications, allergies to medications, social history, cigarette and alcohol use, and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero—first dose of medication(s)).

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3, ICAM-1, sICAM-1, TLR-7;

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNɣ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-ɣ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. For levocetirizine, peak concentrations are typically 270 ng/ml and 308 ng/ml following a single and repeated 5 mg once daily oral dose, respectively. In extreme cases this can be doubled, tripled, otherwise increased. In mild cases, this amount can be halved, quartered, or otherwise reduced.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

Given the half-lives of the molecules and other pharmacokinetic considerations, once oral daily dosing, particularly in an acutely ill patient with nausea and vomiting, may not be effective. As such, particularly in a difficult-to-treat or harsh environment, a long-acting injectable may be employed.

For instance, a long acting injectable comprising 50-100 mg of levocetirizine and 100-200 mg of montelukast within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day for seven days (depending on the nature and extent of the disease process; taking into consideration patient weight, age, etc.). Oral dosing can also be used where appropriate to achieve similar blood levels.

The primary endpoint of the study is the percentage reduction in mortality or symptoms when compared to age and symptom matched controls at time zero as determined from the WHO database. The long-acting injectable is found to decrease in the mortality by up to 90% base on published mortality rates for patients with toxic phase disease with a mean serum concentration level between 350-500 ng/ml. Levels of IL-6 (attenuated by levocetirizine) directly correlate with mortality.

The secondary endpoint is the mean time to clinical resolution.

Patients receiving the levocetirizine and montelukast exhibit less severe symptoms. Patients report, on a pain intensity scale (0-10), headaches, fever, chills and muscle pain are 40% less intense and fatigue is 50% less intense in the EXPT group when compared to the CONT group. Also, 50% fewer patients display vomiting in the EXPT group. Fever levels in EXPT group is an average of 2° F. lower than the CONT group after 2 days of dosing. In patients making a full recovery, the patients in the EXPT group have normal temperatures on average 4 days faster than those in the CONT group.

By day 4 of treatment, viral titers in EXPT patients are, on average, 55% lower than in the CONT group. In patients making a full recovery, the patients in the EXPT group are virus free (by measure of viral titers) on average 4 days faster than those in the CONT group.

Those in the EXPT group have 50% lower incidences of prolonged secondary issues resulting from the acute infection.

Example 7

TBE

Based on the inventor's clinical experience using levocetirizine and montelukast, the following results are projected using controlled studies.

A cohort of 40 patients between the ages of 20-35 years of age (with no other co-morbid viral or disease processes) infected with TBE virus is identified. Each patient is identified as having two or more symptoms of encephalitis or meningitis (and, e.g., fever, headache, malaise, nausea, vomiting, myalgis, and fasiculations). The experimental group patients (n=20; "EXPT") receives levocetirizine and montelukast as well as conventional TBE therapies. The control group patients (n=20; "CONT") receive conventional therapies for treating TBE alone.

Age, sex, race, height, weight, BMI (Body Mass Index/kg/m$^2$), vital signs, major medical problems, medications, allergies to medications, cigarette and alcohol use, social history and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero—first dose of medication(s)).

Screening laboratory studies consisting of a complete blood count, comprehensive metabolic panel, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3;

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN- γ-inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. For levocetirizine, peak concentrations are typically 270 ng/ml and 308 ng/ml following a single and repeated 5 mg once daily oral dose, respectively. In extreme cases this can be doubled, tripled, otherwise increased. In mild cases, this amount can be halved, quartered, or otherwise reduced.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

A long acting injectable comprising 50-100 mg of levocetirizine and 100-200 mg of montelukast within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day for seven days (depending on the nature and extent of the disease process; taking into consideration patient weight, age, etc.). Oral dosing can also be used where appropriate to achieve similar blood levels.

The primary endpoint of the study is the percentage reduction in sequelae of the disease when compared to age and symptom matched controls at time zero as determined from the WHO database. The long-acting injectable is found to decrease the sequelae by of up to 50% base on published data for patients presenting with toxic phase disease. Patients receiving the levocetirizine and montelukast exhibit less severe symptoms; have an average 30% reduction in meningitis duration, 40% reduction in encephalitis duration, and a 50% reduction in the duration of meningoencephalitis in the EXPT group versus those in the CONT group.

By day 4 of treatment, viral titers in EXPT patients are, on average, 55% lower than in the CONT group. In patients making a full recovery, the patients in the EXPT group are virus free (by measure of viral titers) on average 4 days faster than those in the CONT group.

Those in the EXPT group have up to a 50% lower incidence of prolonged secondary issues resulting from the acute infection (asthenia, headache, memory loss, decreased concentration, anxiety, and emotional lability).

Example 8

Malaria

Based on the inventor's clinical experience using levocetirizine and montelukast, the following results are projected using controlled studies.

A cohort of 40 patients between the ages of 20-35 years of age (with no other co-morbid viral or disease processes) infected with Malaria is identified. Each patient is identified as having one or more of symptoms of Malaria (e.g., headache, fever, shivering, joint pain, vomiting, hemolytic anemia, jaundice, hemoglobin in the urine, retinal damage, and convulsions). The experimental group patients (n=20; "EXPT") receives levocetirizine and montelukast as well as conventional Malaria therapies. The control group patients (n=20; "CONT") receive conventional therapies for treating Malaria alone.

Age, sex, race, height, weight, BMI (Body Mass Index/ kg/m$^2$), vital signs, major medical problems, medications, allergies to medications, cigarette and alcohol use, social history and previous surgery are logged at the initial visit and the patient's symptom profile tracked in a controlled environment.

If possible, an applicable quality of life questionnaire is filled out by the patient and health care provider.

Onset, duration, and intensity of symptoms are logged in addition to the time to resolution of symptoms (time zero— first dose of medication(s)).

Screening laboratory studies consisting of a complete blood count, comprehensive metabolic panel, parasite analysis, C-reactive protein, T and B cell lymphocyte panel, chest x-ray, EKG, HIV testing, viral cultures, viral load, blood cultures and aerobic cultures of the airway are taken the time of presentation.

Additional specimens are drawn for analysis:

Once to twice daily serum levels of levocetirizine and montelukast for seven days;

Samples for NF-kB, TLR3, TLR7, TLR9;

Samples for chemokines, cytokines, biomarkers of inflammation, and biomarkers of coagulopathy. These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ-inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Vascular endothelial growth factor A (VEGF-A); D-dimer; Tissue plasminogen activator (TPA); Plasminogen activator inhibitor-1 (PAI-1); Serum amyloid antigen (SAA); Regulated on activation, normal T-cell expressed and secreted (RANTES); sVCAM-1; Fibrinogen; Ferritin; Cortisol; Tissue factor (TF); and Thrombomodulin.

Dosing

In some embodiments, in the treatment of life-threatening disease, sustained tissue levels are used to oversaturate the H1 and leukotriene receptors in order to achieve the desired clinical outcome. For levocetirizine, peak concentrations are typically 270 ng/ml and 308 ng/ml following a single and repeated 5 mg once daily oral dose, respectively. In extreme cases this can be doubled, tripled, otherwise increased. In mild cases, this amount can be halved, quartered, or otherwise reduced.

For montelukast, the pharmacokinetics are nearly linear for oral doses up to 50 mg with safety studies up to 900 mg/day for one week. A standard 10 mg oral dose is reflected by a mean AUC 2689 ng/hr/ml (range 1521 to 4595) and mean Cmax of 353 ng/ml.

A long acting injectable comprising 50-100 mg of levocetirizine and 100-200 mg of montelukast within a pharmaceutically acceptable medium (e.g., reconstituted lyophilized powder) is dosed to maintain a steady state level for seven days. The injectable can be configured to deliver the oral equivalent of between 5 mg and 20 mg of levocetirizine and between 10 mg and 40 mg of montelukast to the patient per day for seven days (depending on the nature and extent of the disease process; taking into consideration patient weight, age, etc.). Oral dosing can also be used where appropriate to achieve similar blood levels.

The primary endpoint of the study is the percentage reduction in mortality or symptoms when compared to age and symptom matched controls at time zero as determined from the WHO database. Patients receiving the levocetirizine and montelukast exhibit less severe symptoms.

Patients receiving the levocetirizine and montelukast exhibit less severe symptoms. Patients report, on a pain intensity scale (0-10), headaches, fever, chills and muscle pain are 20% less intense and fatigue is 30% less intense in the EXPT group when compared to the CONT group. Also, 50% fewer patients display vomiting in the EXPT group. Fever levels in EXPT group is an average of 2° F. than the CONT group after 2 days of dosing. In patients making a full recovery, the patients in the EXPT group have normal temperatures on average 4 days faster than those in the CONT group.

Example 8

HIV

HIV is a single-stranded RNA retrovirus that may present as a mononucleosis type syndrome with a myriad of non-specific symptoms. This constellation of symptoms is also known as the acute retroviral syndrome. The most common findings are fever, lymphadenopathy, sore throat, rash myalgia/arthralgia and headache. None of the findings are specific for acute HIV infection but certain features, especially prolonged duration of symptoms and the presence of mucocutaneous ulcers are suggestive of the diagnosis.

The presence and increased severity and the duration of symptoms appear to be poor prognostic factors. Following HIV seroconversion, each additional symptom present at the time of acute infection is associated with an increasing risk of overall mortality.

The differential diagnosis of acute HIV infection includes mononucleosis due to Epstein-Barr virus, cytomegalic virus (CMV), toxoplasmosis, rubella, syphilis, viral hepatitis, disseminated gonococcal infection, and other infections.

Diagnosis of acute or early HIV infection is established by the detection of HIV viremia in a setting of a particular HIV serological test pattern. Early HIV infection is characterized by markedly elevated HIV RNA levels, easily detectable with the HIV RNA (viral load) assays commonly used for monitoring of HIV disease. In a study of 436 patients with symptoms consistent with acute HIV infection all the 54 patients diagnosed with acute HIV had RNA levels greater than 100,000 copies per ml.

Opportunistic infections are usually associated with later stage HIV disease. Eradication of the latent reservoir of HIV has been a focus of novel interventions aimed at curing the infection.

Population-based studies of the natural history of HIV infection have suggested that the main CD4 cell count is approximately 1000 cells per microliter prior to seroconversion and decreases to 780 cells per microliter at 6 months following seroconversion and to 670 cells per microliter at one year. With depletion of CD4 cells, humoral immunity wanes over time. The acquired immunodeficiency syndrome (AIDS) is the outcome of chronic HIV infection and consequent depletion of CD4 cells. AIDS is defined as a CD4 cell count less than 200 cells per microliter or in the presence of any AIDS defining condition regardless of the CD4 cell count. AIDS defining conditions are opportunistic illnesses that occur more frequently or more severely because of immunosuppression. These include many opportunistic infections, but also certain malignancies as well as conditions without a clear alternative etiology thought to be related to the uncontrolled HIV infection itself such as wasting or encephalopathy.

This case represents a patient with chronic HIV treated with levocetirizine and montelukast over a period of 3 years. During that period on standard retroviral therapy the CD4 count significantly increased. There have been no infections.

HIV receptors: TLR7, TLR8
Name: GT
DOB: Oct. 16, 1951 Age at first visit 55
Date of initial examination: Jan. 15, 2007
HPI: The patient is a 63-year-old male originally seen in the office in 2007 with a diagnosis of chronic sinusitis. The history sinusitis dates back to 2000 at which time he underwent endoscopic sinus surgery at UCLA without improvement.

Symptoms included facial pressure, post nasal drainage, eustachian tube dysfunction, and headaches occurring in the frequency of 2 to 3 times per week, lasting for hours and scaled 5-6/10. Previous allergy testing had the documented sensitivities to mugwort and peanut. A CT Scan of the Sinuses obtained at Santa Barbara cottage Hospital Jan. 5, 2007 demonstrated opacification of the right frontal sinusitis and an osteoma in the left frontal sinus. Initial medical management included daily Nasonex® (mometasone), a steroid nasal spray, Allegra® (fexofenadine) and an immune workup.

Levocetirizine was initiated in October 2007 followed by the addition of montelukast in 2008 Generic levocetirizine utilized in 2012 was switched to 'brand' given the pharmacokinetic and dosing variances encountered with the generic product.

Past Medical/Surgical History
 HIV infection
 Parkinson's disease
 congestive cardiomyopathy
 degenerative disc disease
 hypothyroidism on replacement
 pulmonary embolism September 9
 asthmatic bronchitis
 chronic sinusitis status post surgery 2000
 right shoulder surgery, 2004
 left shoulder surgery, 1996
 low back pain L5-S1 decompression surgery 2013
Medications:
 levocetirizine 5 mg per day
 montelukast 10 mg per day
 aspirin 81 mg orally per day
 Cozaar® (losartan)25 mg per day—ARBs
 carvedilol 6.25 mg twice a day
 spironolactone 25 mg per day
 Duratuss® (dextromethorphan/guaifenesin) 10/200 one daily
 testosterone 200 mg IM weekly
 Epzicom® (300 mg lamivudine/600 mg abacavir) daily for HIV
 Viramune® (nevirapine) 400 mg per day for HIV
 Nasacort (triamcinolone) two puff each nostril bid
 Astelin (azelastine) 2 puffs each nostril bid, as needed
 ropinirole 0.75 mg three times per day Nandrolone 200 mg IM per week Cialis 5 mg per day Atrovent 2 puffs each nostril as needed carisoprodol 350 mg as needed—muscle relaxant hydrocodone/acetaminophen (10 mg/325 mg) as needed for pain Allergies to Medications: ciprofloxacin, Coreg (confusion)

Habits:

Cigarettes—none

Alcohol—none

Occupational history: retired from the film making industry

Review of Systems: Mar. 9, 2015

General: no recent fevers, chills or weight loss.

HEENT: no headache, visual or auditory changes. Chronic sinusitis.

Pulmonary: history of asthmatic bronchitis. No recent cough, sputum, hemostasis, or wheezing Cardiovascular: congestive cardiomyopathy Gastrointestinal: no nausea, vomiting, diarrhea, constipation, history of G.I. bleeding, or peptic ulcer disease.

Genitourinary: no nocturia, dysuria, urgency, frequency, hematuria or decrease stream.

Musculoskeletal: joint pain—shoulder and back

Skin: no recent lesions

Endocrine thyroid disease. No diabetes.

Neurologic: no TIA, CVA or seizures.

Psychiatric: no anxiety or depression.

Objective Findings:

Vital signs: weight 219 pounds, height 6'1", BMI 28.89 kg/m2

B/P 140/84, heart rate 79 and regular, respiratory rate 14 and unlabored.

ENT:

Ears: gray tympanic membranes

Nose: open anterior airway, 2×3.5 cm septal perforation, no evidence infection

Throat: 2+ tonsils, no erythema.

Neck: supple no JVD. Normal carotid pulses, without 3. No thyromegaly

Laboratory Data:

Salient information:
Apr. 30, 2015
Laboratory Data
Pacific Diagnostic Laboratories
89 S. Patterson Ave.
Santa Barbara, Ca. Ca. 93111
CBC
WBC*           7.0 K/uL    normal 4-10
Hgb            15.7 g/dl   normal: 13-17
Hct            47.9%
Platelet count 294 K/uL    normal: 150-450
Comprehensive metabolic panel - normal
CRP            11.1 mg/L   normal <10.0 elevated/very likely cardiac
May 4, 2015
HIV-1 RNA by PCR <20 copies/ml The reportable range for this test is 20-10,000,000.
Jul. 21, 2011    689
CD4 helper
count
2015 CD4 helper  >1100
count Assessment/Summary:

63 year old male with multiple major medical problems as delineated

Congestive cardiomyopathy

HIV

Chronic sinusitis

CD4 helper count stabilized/improved on levocetirizine and montelukast over the past three years with no change in retroviral therapy/HIV-1 RNA by PCR—normal.

No significant interval infection. Note, the patient's Parkinson's disease also stabilized under the combination dose of montelukast and levocetirizine provided.

Based on these clinical results using levocetirizine and montelukast, the following results are projected using controlled studies. Patients using a combination of levocetirizine and montelukast experience delayed progression of HIV, decreased HIV symptoms, reduced incidence of opportunistic infection, and an increased quality of life.

Example 9

Alzheimer's Disease

Based on the inventor's clinical experience using levocetirizine and montelukast, the following results are projected using controlled studies.

Alzheimer's disease is a progressive and fatal neurodegenerative disease affecting motor neurons in the spinal cord, motor cortex, and brain. It is characteristically a disease of older age and exceptional to occur before the age of 60. The incidence and prevalence increase exponentially with age. Cardinal symptoms are memory impairment and often the earliest symptom. Language and visual spatial skills tend to be affected relatively early, while deficits in executive function and behavioral symptoms often manifest later in the disease course.

A cohort of 60 patients with Alzheimer's disease between the ages of 60-70 years of age is identified by both a neurologist and neuropsychiatrist. A detailed cognitive and general neurological examination is paramount, complete with the use of standardized mental status scales, in particular, the Mini-Mental Status Examination (MMSE), to document the progression of dementia and the Montreal Cognitive Assessment (MoCA) owing to its superior sensitivity in detecting mild cognitive impairment and increased sensitivity to executive and language dysfunction. A neurophyschological assessment will establish a baseline in order to follow the patient over time.

The differential diagnosis includes dementia with Lewy bodies parenthesis DLB) which may be the $2^{nd}$ most common type of degenerative dementia after Alzheimer's disease. Clinical features that help distinguish dementia with Lewy bodies from Alzheimer's disease include prominent early appearance of visual hallucinations, along with parkinsonism, cognitive fluctuations, dysautonomia, sleep disorders, and neuroleptic sensitivity.

Routine laboratory tests are generally not useful in the positive diagnosis of Alzheimer's disease; however, some laboratory testing (e.g., complete blood count, comprehensive metabolic panel, thyroid function studies, vitamin B12) are indicated to exclude other/contributing secondary causes.

The experimental group patients (n=20; "EXPT1") receives levocetirizine and montelukast once a day. The experimental group patients (n=20; "EXPT2") receives levocetirizine and montelukast twice a day. The control group patients (n=20; "CONT") receive a placebo Age, sex, race, height, weight, BMI (Body Mass Index/kg/m²), vital signs, major medical problems, medications, allergies to medications, cigarette and alcohol use, social history, and previous surgery are logged at the initial visit and the patient's overall status tracked monthly over one year.

Additional specimens are drawn for analysis:

Serum levels of levocetirizine and montelukast monthly;

Sample for NF-kB, initially and at the conclusion of the study;

Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol; CSF for molecular biomarkers of Aβ protein deposition: CSF Aβ42, total tau and phosphor-tau initially and at the completion of the study.

Imaging: MRI of the brain

Dosing

"EXPT1"—levocetirizine 5 mg, orally at night, montelukast 10 mg orally at night

"EXPT2"—levocetirizine: 2.5 mg orally in the morning and 5.0 mg orally at night plus montelukast: 5 mg orally in the morning and 10 mg orally at night "CONT"—placebo Outcome The clinical course, as measured by the MMSE and Clinical Dementia Rating Scale is not necessarily linear, however, a number of studies have found that patients decline 3 to 3.5 points on the average on the MMS capital E each year, with a minority (<10%) having a more rapidly progressive decline of 5 to 6 points on annual MMSE.

Patients receiving the levocetirizine and montelukast (EXPT1 and EXPT2) remain at baseline or deteriorate more slowly the control group (CONT), based on multiple scales of clinical efficacy.

Patient receiving bid dosing of levocetirizine and montelukast (EXPT2) remain at baseline or deteriorate even more slowly than the group dosed once per day (EXPT1) or (CONT), based on multiple scales of clinical efficacy. The EXPT1 group declines at 20% the rate of the CONT group and the EXPT2 group declines at 15% the rate of the CONT group.

Both (EXPT1) and (EXPT2) have a lower dropout rate than the control group, (CONT) (a dropout rate that is 40% and 20% of that of the CONT group for EXPT1 and EXPT2, respectively)

In summary, levocetirizine and montelukast significantly decreases the rate of clinical deterioration when administered to a group of Alzheimer's patients over one year.

Example 10

Dementia

Based on the inventor's clinical experience using levocetirizine and montelukast, the following results are projected using controlled studies.

Dementia (or senility) is a broad category of brain diseases that cause a long term and often gradual decrease in the ability to think and remember such that a person's daily functioning is affected. This broad category comprises Alzheimer's disease, vascular dementia, Lewy body dementia, and frontotemporal dementia, among others (e.g., normal pressure hydrocephalus, Parkinson's disease, syphilis, and Creutzfeldt-Jakob disease, etc.). Other common symptoms include emotional problems, problems with language, and a decrease in motivation. For the diagnosis to be present it must be a change from a person's usual mental functioning and a greater decline than one would expect due to aging. The incidence and prevalence increase with age. Cardinal symptoms are memory impairment and often the earliest symptom. Language and visual spatial skills tend to be affected relatively early, while deficits in executive function and behavioral symptoms often manifest later in the disease course.

A cohort of 60 patients with dementia between the ages of 60-70 years of age is identified by both a neurologist and neuropsychiatrist. A detailed cognitive and general neurological examination is paramount, complete with the use of standardized mental status scales, in particular, the Mini-Mental Status Examination (MMSE), to document the progression of dementia and the Montreal Cognitive Assessment (MoCA) owing to its superior sensitivity in detecting mild cognitive impairment and increased sensitivity to executive and language dysfunction. A neurophyschological assessment will establish a baseline in order to follow the patient over time.

The experimental group patients (n=20; "EXPT1") receives levocetirizine and montelukast once a day. The experimental group patients (n=20; "EXPT2) receives levocetirizine and montelukast twice a day. The control group patients (n=20; "CONT") receive a placebo.

Age, sex, race, height, weight, BMI (Body Mass Index/kg/m²), vital signs, major medical problems, medications, allergies to medications, cigarette and alcohol use, social history, and previous surgery are logged at the initial visit and the patient's overall status tracked monthly over one year.

Additional specimens are drawn for analysis, which include:

Serum levels of levocetirizine and montelukast monthly;

Sample for NF-kB, initially and at the conclusion of the study;

Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol;

CSF for molecular biomarkers of Aβ protein deposition: CSF Aβ42, total tau and phosphor-tau initially and at the completion of the study.

Imaging: MRI of the brain

Dosing

"EXPT1"—levocetirizine 5 mg, orally at night, montelukast 10 mg orally at night

"EXPT2"—levocetirizine: 2.5 mg orally in the morning and 5.0 mg orally at night plus montelukast: 5 mg orally in the morning and 10 mg orally at night "CONT"—placebo Outcome The clinical course, as measured by the MMSE and Clinical Dementia Rating Scale is not necessarily linear, however, a number of studies have found that patients decline 3 to 3.5 points on the average on the MMS capital E each year, with a minority (<10%) having a more rapidly progressive decline of 5 to 6 points on annual MMSE.

Patients receiving the levocetirizine and montelukast (EXPT1 and EXPT2) remain at baseline or deteriorate more slowly the control group (CONT), based on multiple scales of clinical efficacy. Patient receiving bid dosing of levocetirizine and montelukast (EXPT2) remain at baseline or deteriorate even more slowly than the group dosed once per day (EXPT1) or (CONT), based on multiple scales of clinical efficacy. The EXPT1 group declines at 20% the rate of the CONT group and the EXPT2 group declines at 15% the rate of the CONT group.

Both (EXPT1) and (EXPT2) have a lower dropout rate than the control group, (CONT) (a dropout rate that is 40% and 20% of that of the CONT group for EXPT1 and EXPT2, respectively)

In summary, levocetirizine and montelukast significantly decreases the rate of clinical deterioration when administered to a group of dementia patients over one year.

Example 11

Dementia With Lewy Bodies

Based on the inventor's clinical experience using levocetirizine and montelukast, the following results are projected using controlled studies.

Dementia with Lewy Bodies (LBD) is a form of dementia closely associated with Parkinson's disease. It is characterized anatomically by the presence of Lewy bodies, clumps of alpha-synuclein and ubiquitin protein in neurons, detectable in post mortem brain histology. LBD is a progressive degenerative dementia primarily affecting older adults that manifests as cognitive decline, which can lead to hallucinations, as well as varied attention and alertness when compared to a person's baseline function. Persons with LBD display an inability to plan or a loss of analytical or abstract thinking and show markedly fluctuating cognition. Often wakefulness varies from day to day, and alertness and short-term memory rise and fall. REM sleep behavior disorder (RBD) is a symptom often first recognized by the patient's caretaker. RBD includes vivid dreaming, with persistent dreams, purposeful or violent movements, and falling out of bed. Persistent or recurring visual hallucinations with vivid and detailed pictures are often an early diagnostic symptom. LBD symptoms overlap clinically with Alzheimer's disease and Parkinson's disease, but are more commonly associated with the latter. Because of this overlap, LBD in its early years is often misdiagnosed.

A cohort of 60 patients with LBD between the ages of 60-70 years of age is identified by both a neurologist and neuropsychiatrist. A detailed cognitive and general neurological examination is paramount, complete with the use of standardized mental status scales, in particular, the Mini-Mental Status Examination (MMSE), to document the progression of LBD and the Montreal Cognitive Assessment (MoCA) owing to its superior sensitivity in detecting mild cognitive impairment and increased sensitivity to executive and language dysfunction. A neurophyschological assessment will establish a baseline in order to follow the patient over time.

The experimental group patients (n=20; "EXPT1") receives levocetirizine and montelukast once a day. The experimental group patients (n=20; "EXPT2) receives levocetirizine and montelukast twice a day. The control group patients (n=20; "CONT") receive a placebo.

Age, sex, race, height, weight, BMI (Body Mass Index/ $kg/m^2$), vital signs, major medical problems, medications, allergies to medications, cigarette and alcohol use, social history, and previous surgery are logged at the initial visit and the patient's overall status tracked monthly over one year.

Additional specimens are drawn for analysis, which include:

Serum levels of levocetirizine and montelukast monthly;

Sample for NF-kB, initially and at the conclusion of the study;

Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNϒ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-ϒ-inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol; CSF for molecular biomarkers of Aβ protein deposition: CSF Aβ42, total tau and phosphor-tau initially and at the completion of the study.

Imaging: MRI of the brain

Dosing

"EXPT1"—levocetirizine 5 mg, orally at night, montelukast 10 mg orally at night

"EXPT2"—levocetirizine: 2.5 mg orally in the morning and 5.0 mg orally at night plus montelukast: 5 mg orally in the morning and 10 mg orally at night "CONT"—placebo Outcome The clinical course, as measured by the MMSE and Clinical Dementia Rating Scale is not necessarily linear, however, a number of studies have found that patients decline 3 to 3.5 points on the average on the MMS capital E each year, with a minority (<10%) having a more rapidly progressive decline of 5 to 6 points on annual MMSE.

Patients receiving the levocetirizine and montelukast (EXPT1 and EXPT2) remain at baseline or deteriorate more slowly the control group (CONT), based on multiple scales of clinical efficacy. Patient receiving bid dosing of levocetirizine and montelukast (EXPT2) remain at baseline or deteriorate even more slowly than the group dosed once per day (EXPT1) or (CONT), based on multiple scales of clinical efficacy. The EXPT1 group declines at 10% the rate of the CONT group and the EXPT2 group declines at 5% the rate of the CONT group.

Both (EXPT1) and (EXPT2) have a lower dropout rate than the control group, (CONT) (a dropout rate that is 40% and 20% of that of the CONT group for EXPT1 and EXPT2, respectively)

In summary, levocetirizine and montelukast significantly decreases the rate of clinical deterioration when administered to a group of LBD patients over one year.

Example 12

Parkinson's Disease

Based on the inventor's clinical experience using levocetirizine and montelukast, the following results are projected using controlled studies.

Parkinson's Disease (also known as idiopathic or primary parkinsonism, hypokinetic rigid syndrome, or paralysis agitans) is a degenerative disorder of the central nervous system mainly affecting the motor system. Parkinson's disease may manifest from the death of dopamine-generating cells in the substantia nigra, a region of the midbrain. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease, whereas depression is the most common psychiatric symptom. Other symptoms include sensory, sleep and emotional problems. Parkinson's disease is more common in older people, with most cases occurring after the age of 50; when it is seen in young adults, it is called young onset Parkinson's Disease.

The main motor symptoms are collectively called parkinsonism, or a "parkinsonian syndrome." The disease can be either primary or secondary. Primary Parkinson's disease is referred to as idiopathic (having no known cause), although some atypical cases have a genetic origin, while secondary parkinsonism is due to known causes, e.g., toxins. Many risks and protective factors have been investigated: the clearest evidence is an increased risk of Parkinson's in people exposed to certain pesticides and a reduced risk in tobacco smokers. The pathology of the disease is characterized by the accumulation of protein in neurons (Lewy bodies), and from insufficient formation and activity of dopamine in certain parts of the midbrain. The location of the Lewy bodies is often related to the expression and degree of the symptoms of an individual. Diagnosis of typical cases is mainly based on symptoms, with tests such as neuroimaging used for confirmation.

A cohort of 60 patients with Parkinson's disease between the ages of 40-65 years of age is identified by both a neurologist and neuropsychiatrist. A detailed motor, cognitive, and general neurological examination is paramount, complete with the use of standardized motor status scales, mental status scales, in particular, the Mini-Mental Status Examination (MMSE), to document the progression of Parkinson's and the Montreal Cognitive Assessment (MoCA) owing to its superior sensitivity in detecting mild cognitive impairment and increased sensitivity to executive and language dysfunction. A neurophyschological assessment will establish a baseline in order to follow the patient over time.

The experimental group patients (n=20; "EXPT1") receives levocetirizine and montelukast once a day. The experimental group patients (n=20; "EXPT2) receives levocetirizine and montelukast twice a day. The control group patients (n=20; "CONT") receive a placebo.

Age, sex, race, height, weight, BMI (Body Mass Index/ $kg/m^2$), vital signs, major medical problems, medications, allergies to medications, cigarette and alcohol use, social history, and previous surgery are logged at the initial visit and the patient's overall status tracked monthly over one year.

Additional specimens are drawn for analysis, which include:

Serum levels of levocetirizine and montelukast monthly;
Sample for NF-kB, initially and at the conclusion of the study;

Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol; CSF for molecular biomarkers of Aβ protein deposition: CSF Aβ42, total tau and phosphor-tau initially and at the completion of the study.

Imaging: MRI of the brain

Dosing

"EXPT1"—levocetirizine 5 mg, orally at night, montelukast 10 mg orally at night

"EXPT2"—levocetirizine: 2.5 mg orally in the morning and 5.0 mg orally at night plus montelukast: 5 mg orally in the morning and 10 mg orally at night "CONT"—placebo Outcome The clinical course, as measured by the MMSE and Clinical Dementia Rating Scale is not necessarily linear, however, a number of studies have found that patients decline 3 to 3.5 points on the average on the MMS capital E each year, with a minority (<10%) having a more rapidly progressive decline of 5 to 6 points on annual MMSE. Standardized motor testing is also performed.

Patients receiving the levocetirizine and montelukast (EXPT1 and EXPT2) remain at baseline or deteriorate more slowly the control group (CONT), based on multiple scales of clinical efficacy (cognitive and motor). Patient receiving bid dosing of levocetirizine and montelukast (EXPT2) remain at baseline or deteriorate even more slowly than the group dosed once per day (EXPT1) or (CONT), based on multiple scales of clinical efficacy. The EXPT1 group declines at 15% the rate of the CONT group (both cognitively and for motor function) and the EXPT2 group declines at 5% the rate of the CONT group (both cognitively and for motor function).

Both (EXPT1) and (EXPT2) have a lower dropout rate than the control group, (CONT) (a dropout rate that is 30% and 20% of that of the CONT group for EXPT1 and EXPT2, respectively)

In summary, levocetirizine and montelukast significantly decreases the rate of clinical deterioration when administered to a group of Parkinson's patients over one year.

Example 13

Huntington's Disease

Based on the inventor's clinical experience using levocetirizine and montelukast, the following results are projected using controlled studies.

Huntington's disease (HD) is a neurodegenerative genetic disorder that affects muscle coordination and leads to mental decline and behavioral symptoms. Symptoms of the disease can vary between individuals and affected members of the same family, but usually progress predictably. The earliest symptoms are often subtle problems with mood or cognition. A general lack of coordination and an unsteady gait often follows. As the disease advances, uncoordinated, jerky body movements become more apparent, along with a decline in mental abilities and behavioral symptoms. Physical abilities gradually worsen until coordinated movement becomes difficult. Mental abilities generally decline into dementia. Complications such as pneumonia, heart disease, and physical injury from falls reduce life expectancy to around twenty years from the point at which symptoms begin. Physical symptoms can begin at any age from infancy to old age, but usually begin between 35 and 44 years of age. The disease may develop earlier in life in each successive generation. About 6% of cases start before the age of 21 years with an akinetic-rigid syndrome; they progress faster and vary slightly. The variant is classified as juvenile, akinetic-rigid, or Westphal variant HD.

A cohort of 60 patients with Huntington's disease between the ages of 30-45 years of age is identified by both a neurologist and neuropsychiatrist. A detailed motor, cognitive, and general neurological examination is paramount, complete with the use of standardized motor and mental status testing. A motor, muscular, and neurophyschological assessment will establish a baseline in order to follow the patient over time.

The experimental group patients (n=20; "EXPT1") receives levocetirizine and montelukast once a day. The experimental group patients (n=20; "EXPT2") receives levocetirizine and montelukast twice a day. The control group patients (n=20; "CONT") receive a placebo.

Age, sex, race, height, weight, BMI (Body Mass Index/ $kg/m^2$), vital signs, major medical problems, medications, allergies to medications, cigarette and alcohol use, social history, and previous surgery are logged at the initial visit and the patient's overall status tracked monthly over one year.

Additional specimens are drawn for analysis, which include:

Genetic molecular testing for HD
Serum levels of levocetirizine and montelukast monthly;
Sample for NF-kB, initially and at the conclusion of the study;
Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNɣ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-ɣ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol;
Imaging: MRI of the brain Dosing
"EXPT1"—levocetirizine 5 mg, orally at night, montelukast 10 mg orally at night
"EXPT2"—levocetirizine: 2.5 mg orally in the morning and 5.0 mg orally at night plus montelukast: 5 mg orally in the morning and 10 mg orally at night
"CONT"—placebo Outcome Patients receiving the levocetirizine and montelukast (EXPT1 and EXPT2) remain at baseline or deteriorate more slowly the control group (CONT), based on multiple scales of clinical efficacy (both cognitive and motor). Patient receiving bid dosing of levocetirizine and montelukast (EXPT2) remain at baseline or deteriorate even more slowly than the group dosed once per day (EXPT1) or (CONT), based on multiple scales of clinical efficacy (both cognitive and motor). The EXPT1 group declines at 25% the rate of the CONT group (both cognitively and for motor function) and the EXPT2 group declines at 20% the rate of the CONT group (both cognitively and for motor function).

Both (EXPT1) and (EXPT2) have a lower dropout rate than the control group, (CONT) (a dropout rate that is 30% and 20% of that of the CONT group for EXPT1 and EXPT2, respectively)

In summary, levocetirizine and montelukast significantly decreases the rate of clinical deterioration when administered to a group of Huntington's patients over one year.

Example 14

Amyotrophic Lateral Sclerosis (ALS)

Based on the inventor's clinical experience using levocetirizine and montelukast, the following results are projected using controlled studies.

Amyotrophic lateral sclerosis (ALS) is a disorder that involves the death of neurons. ALS is characterized by stiff muscles, muscle twitching, and gradually worsening weakness due to muscle wasting. This results in difficulty speaking, swallowing, and eventually breathing. About 5-10% of cases are inherited from a person's parents. About half of these genetic cases are due to one of two specific genes. Recently, ALS has been correlated with repeated head injury with resultant death of the neurons that control voluntary muscles. The diagnosis is based on a person's signs and symptoms with testing done to rule out other potential causes.

The disease usually starts around the age of 60 and in inherited cases around the age of 50. The average survival from onset to death is three to four years. About 10% survive longer than 10 years. Most die from respiratory failure.

A cohort of 60 patients with ALS between the ages of 45 and 60 years of age is identified by both a physician. A detailed motor and general neurological examination is paramount, complete with the use of standardized motor testing (e.g., EMG—electromyogram and nerve conduction studies), to document the progression of ALS. This establishes a patient baseline.

The experimental group patients (n=20; "EXPT1") receives levocetirizine and montelukast once a day. The experimental group patients (n=20; "EXPT2") receives levocetirizine and montelukast twice a day. The control group patients (n=20; "CONT") receive a placebo.

Age, sex, race, height, weight, BMI (Body Mass Index/ kg/m²), vital signs, major medical problems, medications, allergies to medications, cigarette and alcohol use, social history, and previous surgery are logged at the initial visit and the patient's overall status tracked monthly over one year.

Additional specimens are drawn for analysis, which include:

Serum levels of levocetirizine and montelukast monthly;
Sample for NF-kB, initially and at the conclusion of the study;
Samples for chemokines, cytokines, and biomarkers of inflammation at the time of entry into the study and at completion (52 weeks). These include but are not limited to: Granulocyte macrophage colony stimulating factor (GM-CSF); GROα; Interferon α2 (IFNα2); IFNβ; IFNγ; IL-10; Interleukin 12p'70 (IL-12p70); IL12p40; Interleukin 1α (IL-1α); IL-1β; IL-1 receptor antagonist (IL-1RA); IL-2; IL-4; IL-5; IL-6; IL-8; IFN-γ -inducible protein 10 (IP-10); Monocyte chemoattractant protein 1 (MCP-1); Macrophage colony stimulating factor (MCSF); MIP-α; MIP-1β; Soluble CD40 ligand (sCD40L); Soluble E-selectin (sE-selectin); Soluble Fas ligand (sFasL); Tumor necrosis factor α (TNF-α); Serum amyloid antigen (SAA); regulated on activation, normal T-cell expressed and secreted (RANTES); Cortisol.

Imaging: MRI of the brain

Dosing

"EXPT1"—levocetirizine 5 mg, orally at night, montelukast 10 mg orally at night

"EXPT2"—levocetirizine: 2.5 mg orally in the morning and 5.0 mg orally at night plus montelukast: 5 mg orally in the morning and 10 mg orally at night "CONT"—placebo Outcome Patients receiving the levocetirizine and montelukast (EXPT1 and EXPT2) remain at baseline or deteriorate more slowly the control group (CONT), based on multiple scales of clinical efficacy and electrodiagnostic testing. Patient receiving bid dosing of levocetirizine and montelukast (EXPT2) remain at baseline or deteriorate even more slowly than the group dosed once per day (EXPT1) or (CONT), based on multiple scales of clinical efficacy and electrodiagnostic testing. The EXPT1 group declines at 25% the rate of the CONT group (clinical and electodiagnostic testing) and the EXPT2 group declines at 20% the rate of the CONT group (clinical and electrodiagnostic testing).

Both (EXPT1) and (EXPT2) have a lower dropout rate than the control group, (CONT) (a dropout rate that is 30% and 20% of that of the CONT group for EXPT1 and EXPT2, respectively)

In summary, levocetirizine and montelukast significantly decreases the rate of clinical deterioration when administered to a group of ALS patients over one year.

What is claimed is:

1. A method of treating an NFκB-mediated mediated condition comprising administering to a patient an effective amount of a combination of levocetirizine and montelukast.

2. The method of claim 1, wherein the condition is a neurological disease.

3. The method of claim 1, wherein the condition is selected from the group consisting of Alzheimer's disease, dementia, dementia with Lewy bodies, Parkinson's disease, amyotrophic lateral sclerosis, frontotemporal dementia, and Huntington's disease.

4. The method of claim 1, wherein the condition is caused by a viral infection.

5. The method of claim 1, wherein the condition is caused by a virus selected from the group consisting of the Ebola virus, the West Nile virus, the Yellow Fever virus, the Dengue virus, the tick-borne-encephalitis virus, and HIV.

6. The method of claim 1, wherein the combination of levocetirizine and montelukast is administered in a sequential manner.

7. The method of claim 1, wherein the combination of levocetirizine and montelukast is administered in a substantially simultaneous manner.

8. The method of claim 1, wherein the combination is administered to the patient by one or more of the routes consisting of enteral, intravenous, intraperitoneal, inhalation, intramuscular, subcutaneous and oral.

9. The method of claim 1, wherein the levocetirizine and montelukast are administered by the same route.

10. The method of claim 1, wherein the levocetirizine and montelukast are administered via different routes.

11. The method of claim 1, wherein one or more of levocetirizine or montelukast are provided as a slow release composition.

12. The method of claim 3, wherein the combination further comprises other medications known for use in treating one of the listed conditions.

13. The method of claim 5, wherein the combination further comprises other medications known for use in treating one of the listed viruses.

14. The method of claim 1, wherein the combination further comprises a steroid.

15. The method of claim 1, wherein the NFκB-mediated condition is a viral infection.

16. A method of treating a neurodegenerative disease comprising administering to a patient an effective amount of a combination of levocetirizine and montelukast.

* * * * *